US012569698B1

(12) United States Patent
Madkhali et al.

(10) Patent No.: US 12,569,698 B1
(45) Date of Patent: Mar. 10, 2026

(54) MAGNETIC HYPERTHERMIA THERAPY FOR CANCER TREATMENT

(71) Applicant: IMAM MOHAMMAD IBN SAUD ISLAMIC UNIVERSITY, Riyadh (SA)

(72) Inventors: Nawal Ahmed Madkhali, Riyadh (SA); Saja Mohammed Algessair, Riyadh (SA); Marwan Mohammed Abduljawad, Riyadh (SA); Rizwan Ali, Riyadh (SA); O. Mohamed Lemine, Riyadh (SA)

(73) Assignee: IMAM MOHAMMAD IBN SAUD ISLAMIC UNIVERSITY, Riyadh (SA)

( * ) Notice: Subject to any disclaimer, the term of this patent is extended or adjusted under 35 U.S.C. 154(b) by 0 days.

(21) Appl. No.: 18/984,749

(22) Filed: Dec. 17, 2024

(51) Int. Cl.
    *A61N 2/00* (2006.01)

(52) U.S. Cl.
    CPC .................................... *A61N 2/004* (2013.01)

(58) Field of Classification Search
    None
    See application file for complete search history.

(56) References Cited

U.S. PATENT DOCUMENTS

| | | | | | |
|---|---|---|---|---|---|
| 9,480,978 | B1 * | 11/2016 | Shaikh | .................. | B01J 31/2409 |
| 2007/0059705 | A1 * | 3/2007 | Lu | ........................ | G01N 33/588 |
| | | | | | 435/6.12 |

| | | | | | |
|---|---|---|---|---|---|
| 2010/0129478 | A1 * | 5/2010 | Patell | .................. | A61K 36/185 |
| | | | | | 424/769 |
| 2011/0104073 | A1 * | 5/2011 | Zeng | ........................ | B82Y 5/00 |
| | | | | | 427/127 |
| 2011/0287035 | A1 * | 11/2011 | Peyman | ............. | A61K 41/0028 |
| | | | | | 424/178.1 |

(Continued)

FOREIGN PATENT DOCUMENTS

| | | |
|---|---|---|
| BR | 102016015484 A2 | 1/2018 |
| CN | 106390120 B | 1/2018 |

(Continued)

OTHER PUBLICATIONS

Hilger, I., Hiergeist, R., & Hergt, R. (2002). Thermal ablation of tumors using magnetic nanoparticles. Investigative Radiology, 37(10), 580-586. https://doi.org/10.1097/00004424-200210000-00008 (Year: 2002).*

(Continued)

*Primary Examiner* — Charles A Marmor, II
*Assistant Examiner* — Marc D. Honrath
(74) *Attorney, Agent, or Firm* — Oblon, McClelland, Maier & Neustadt, L.L.P.

(57) ABSTRACT

A method of treating a cancer with magnetic hyperthermia therapy includes heating an aqueous metal chloride mixture to a temperature of 60° C. to 100° C. and reacting the aqueous metal chloride mixture with an ammonia hydroxide solution to obtain metal oxide nanoparticles. The method further includes sonicating a buffered aqueous suspension of the metal oxide nanoparticles and a *Nigella sativa*-derived melanin to obtain melanin-coated magnetite nanoparticles (Mel-MNPs), contacting the Mel-MNPs with the cancer, and applying an external alternating magnetic field to the Mel-MNPs to generate heat and to hyperthermically treat the cancer.

20 Claims, 10 Drawing Sheets

(56) References Cited

U.S. PATENT DOCUMENTS

| | | | | |
|---|---|---|---|---|
| 2012/0241693 | A1* | 9/2012 | Magdassi | B82Y 30/00 |
| | | | | 977/773 |
| 2012/0302819 | A1* | 11/2012 | Alphandery | A61N 1/406 |
| | | | | 424/646 |
| 2015/0132231 | A1* | 5/2015 | Ko | A61K 49/1839 |
| | | | | 424/9.322 |
| 2021/0393798 | A1* | 12/2021 | El-Boubbou | A61K 47/6923 |

FOREIGN PATENT DOCUMENTS

| | | | |
|---|---|---|---|
| RU | 2792161 | C2 * | 3/2023 |
| WO | 2015038924 | A1 | 3/2015 |
| WO | WO-2018150266 | A1 * | 8/2018 ......... A61K 41/0052 |

OTHER PUBLICATIONS

Abdelhalim, M. A., Moussa, S. A., & Qaid, H. (2018). Effect of melanin on gold nanoparticle-induced hepatotoxicity and lipid peroxidation in rats. International Journal of Nanomedicine, vol. 13, 5207-5213. https://doi.org/10.2147/ijn.s170758 (Year: 2018 ).*

Kurian, N. K. (2022). Extraction and Purification of Melanin from Various Cells and Tissues. https://doi.org/10.20944/preprints202205.0375.v1 (Year: 2022).*

El-Boubbou, K., Lemine, O. M., Algessair, S., Madkhali, N., Al-Najar, B., & Ali, R. (2024). Preparation and characterization of various PVPylated divalent metal-doped ferrite nanoparticles for magnetic hyperthermia. RSC Advances, 14(22), 15664-15679. https://doi.org/10.1039/d4ra01600a (Year: 2024).*

Shanmugam, R., Tharani, M., & Abullais, S. S. (2024). Black seed assisted synthesis, characterization, free radical scavenging, antimicrobial and anti-inflammatory activity of iron oxide nanoparticles. BMC Complementary Medicine and Therapies, 24(1). https://doi.org/10.1186/s12906-024-04552-9 (Year: 2024).*

Iron Oxide Nanoparticles Synthesis—(Fe3O4) by using Iron Chloride and Ammonia via Coprecipitation Method—InstaNANO. https://instanano.com/all/nanomaterial-synthesis/metal-oxide/iron-oxide-nanoparticles-1/ (accessed Dec. 1, 2024). (Year: 2024).*

Junqing Wang, et al., "Eumelanin-Fe304 hybrid nanoparticles for enhanced MR/PA imaging-assisted local photothermolysis", Biomaterials Science, vol. 6, Issue 3, Jan. 17, 2018, 586-595, 11 pages.

Tao Feng, et al., "Dual-stimuli responsive nanotheranostics for mild hyperthermia enhanced inhibition of Wnt/β-catenin signaling", Biomaterials, vol. 232, Feb. 2020, 10 Pages.

Kowichi Jimbow, et al., "Melanin biology and translational research strategy; melanogenesis and nanomedicine as the basis for melanoma-targeted DDS and chemothermoimmunotherapy", Pigment Cell & Melanoma Research, vol. 21, Issue 2, Apr. 2008, 243-244, 3 Pages.

* cited by examiner

50

MAGNETIC HYPERTHERMIA THERAPY FOR CANCER TREATMENT

BACKGROUND

Technical Field

The present disclosure is directed toward cancer treatment therapies, and more particularly, towards a magnetic hyperthermia therapy for cancer cell treatments.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Cancer remains a leading cause of mortality globally, with traditional treatments such as chemotherapy, radiotherapy, and surgical interventions being difficult due to known systemic toxicities and suboptimal efficacy. Magnetic hyperthermia involves locally heating cancer cells to the point of destruction. Heat is generated by delivering magnetic nanoparticles (MNPs) to a tumor and applying an alternating magnetic filed (AMF) to the MNPs. Magnetic hyperthermia therapy has emerged as a promising alternative to traditional cancer treatments because the therapy is localized, making it more safe for healthy cells surrounding the cancerous cells, and is generally well tolerated by patients. Further, magnetic hyperthermia therapy has shown promise in treating malignancies that are difficult to manage, such as pancreatic, ovarian, and brain cancers, offering the potential for enhanced therapeutic efficacy and reduced toxicity.

Due to the physicochemical properties of nanoparticles, including nanoscale size, large surface area, and tunable surface chemistry, MNPs enable precise and targeted delivery of therapeutic agents to malignant cancer cells, potentially reducing collateral damage to healthy tissues. As a result, enhancing the heating efficiency of MNPs and subsequent assemblies under magnetic field influence is an active and ongoing research topic. Further, there is a need for biocompatible MNPs that provide accurate temperature control while also reducing the risk of systemic toxicity and damage to surrounding health tissues/cells.

Accordingly, one object of the present disclosure is to provide a method of cancer treatment via magnetic hyperthermia, that may circumvent the drawbacks and limitations of materials known in the art, such as poor biocompatibility, high toxicity, and inadequate temperature control.

SUMMARY

In an exemplary embodiment, a method of treating a cancer with magnetic hyperthermia therapy is described. The method comprises heating an aqueous metal chloride mixture to a temperature of 60° C. to 100° C. and reacting the aqueous metal chloride mixture with an ammonia hydroxide solution to obtain metal oxide nanoparticles. The method further comprises sonicating a buffered aqueous suspension of the metal oxide nanoparticles and a *Nigella sativa*-derived melanin to obtain melanin-coated magnetite nanoparticles (Mel-MNPs), contacting the Mel-MNPs with the cancer, and applying an external alternating magnetic field to the Mel-MNPs to generate heat and to hyperthermically treat the cancer. The cancer is at least one cancer cell line selected from the group consisting of MDAMB231 and KAIMRC1.

In some embodiments the Mel-MNPs have an average particle diameter of 10 nanometers (nm) or less.

In some embodiments, the aqueous metal chloride mixture comprises at least one metal chloride selected from the group consisting of $FeCl_3$, $FeCl_2$, $CoCl_2$, $KCl$, $NH_4Cl$, $MgCl_2$, $NaCl$, $BrCl_2$, $CaCl_2$, $NiCl_2$, and $SrCl_2$.

In some embodiments, the administering comprises administering a composition including the Mel-MNPs in a concentration of at least 3 mg/mL to the cancer.

In some embodiments, the aqueous metal chloride mixture comprises at least one metal chloride selected from the group consisting of $FeCl_3$ and $FeCl_2$.

In some embodiments, the cancer is the cell line MDAMB231.

In some embodiments, the cancer is the cell line KAIMRC1.

In some embodiments, the Mel-MNPs have a remanence of 0.05 electromagnetic unit per gram (emu/g) to 1 emu/g.

In some embodiments, the external alternating magnetic field has a frequency of 300 kilohertz (kHZ) to 700 kHz.

In some embodiments, the Mel-MNPs have a magnetic coercivity ($H_C$) of 4.5 Oersted to 6.5 Oersted (Oe).

In some embodiments, the buffered aqueous suspension comprises at least one selected from the group consisting of (4-(2-hydroxyethyl)-1-piperazineethanesulfonic acid (HEPES), 3-(N-morpholino)propanesulfonic acid (MOPS), and tris(hydroxymethyl)aminomethane hydrochloride (TRIS—HCl).

In some embodiments, the Mel-MNPs have an average particle diameter of 6.5 nm or less.

In some embodiments, the sonicating comprises sonicating the buffered aqueous suspension for 10 to 40 minutes at a frequency of 15 kHz to 50 kHz to obtain the Mel-MNPs.

In some embodiments, the method further comprises solubilizing black seed coats of *Nigella sativa* in an NaOH solution for at least 2 hours to obtain an extract solution, centrifuging the extract solution at a rate of 1000 to 4000 revolutions per minute (rpm) for 1 to 10 minutes, then adding an HCl solution to obtain a precipitate, and filtering the precipitate to obtain the *Nigella sativa*-derived melanin.

In some embodiments, the Mel-MNPs have a saturation magnetization ($M_S$) of 6.5 emu/g to 9 emu/g.

In some embodiments, the buffered aqueous suspension has a weight ratio of metal oxide nanoparticles to *Nigella sativa*-derived melanin of 1:15 to 15:1.

In some embodiments, the administering comprises administering a composition including the Mel-MNPs in a concentration of at least 10 mg/mL to the cancer.

In some embodiments, the buffered aqueous suspension has a weight ratio of metal oxide nanoparticles to *Nigella sativa*-derived melanin of 10:1.

In some embodiments, the applying of the external alternating magnetic field to the Mel-MNPs in the cancer achieves an internal temperature of the cancer of at least 45° C. in 10 minutes or less at a frequency of 300 to 700 kHz.

In some embodiments, the applying of the external alternating magnetic field to the Mel-MNPs in the cancer achieves an internal temperature of the cancer of at least 55° C. in 5 minutes or less at a frequency of 300 to 400 kHz.

The foregoing general description of the illustrative embodiments and the following detailed description thereof are merely exemplary aspects of the teachings of this disclosure and are not restrictive.

BRIEF DESCRIPTION OF DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
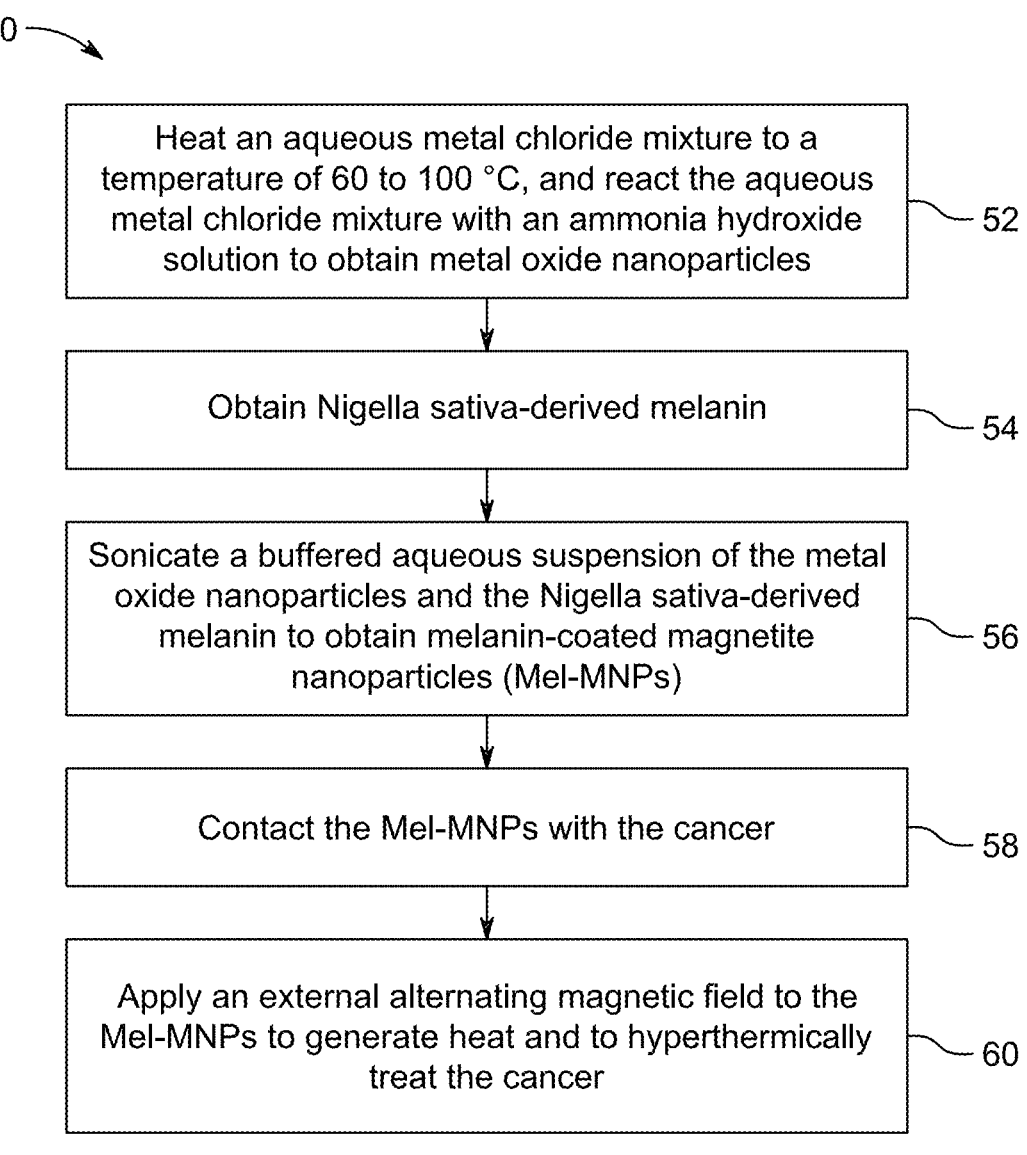
FIG. 1 is an exemplary flow chart of a method of treating a cancer with magnetic hyperthermia therapy, according to certain embodiments.

Embodiments of the present disclosure will now be described more fully hereinafter with reference to the accompanying drawings, in which some, but not all embodiments of the disclosure are shown.

The present disclosure will be better understood with reference to the following definitions. As used herein, the words "a" and "an" and the like carry the meaning of "one or more." Within the description of this disclosure, where a numerical limit or range is stated, the endpoints are included unless stated otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the words "about," "approximately," or "substantially similar" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), or +/−20% of the stated value (or range of values). Within the description of this disclosure, where a numerical limit or range is stated, the endpoints are included unless stated otherwise. Also, all values and subranges within a numerical limit or range are specifically included as if explicitly written out.

The present disclosure is intended to include all hydration states of a given compound or formula, unless otherwise noted or when heating a material.

In addition, the present disclosure is intended to include all isotopes of atoms occurring in the present compounds and complexes. Isotopes include those atoms having the same atomic number but different mass numbers. By way of general example, and without limitation, isotopes of hydrogen include deuterium and tritium. Isotopically labelled compounds of the disclosure may generally be prepared by conventional techniques known to those skilled in the art or by processes analogous to those described herein, using an appropriate isotopically labelled reagent in place of the non-labelled reagent otherwise employed.

As used herein, the terms "optional" or "optionally" means that the subsequently described event(s) can or cannot occur or the subsequently described component(s) may or may not be present (e.g., 0 wt. %).

As used herein, "remanence" refers to the magnetic field that remains in a material after an external magnetic field is removed. A high remanence indicates a strong magnetic field persists even without an external field, making it ideal for permanent magnets, while a low remanence indicates a weaker magnetic field remaining after the external field is removed, beneficial in applications where quick magnetization changes are needed. For magnetic hyperthermia cancer treatment, low remanence is generally considered better than high remanence because low remanence indicates a "soft magnetic material" or "superparamagnetic nanoparticles", which is more efficient at generating heat when exposed to an alternating magnetic field, minimizing unwanted residual magnetism, and allowing for better control over the heating process within the tumor tissue.

As used herein, "soft magnetic material" refers to materials with low remanence, meaning they easily magnetize and demagnetize when exposed to a changing magnetic field.

As used herein, "superparamagnetic nanoparticles" refers to materials with very low or negligible remanence, meaning they easily magnetize and demagnetize when exposed to a changing magnetic field.

As used herein, "saturation magnetization" is the maximum amount of magnetization that a magnetic material can achieve when exposed to an external magnetic field. It occurs when the material's magnetization can't be increased any further, even if the external magnetic field is increased. The saturation magnetization of a material decreases as the size of the material is reduced. For hyperthermia applications, a high saturation magnetization is preferred because it results in large thermal energy dissipation in the tumor cells and increased control on the movement of the magnetic nanoparticles in the blood using external magnetic field.

As used herein, "trace amount" refers to a very small quantity, typically less than 0.1 wt. % and not usually specified with a precise percentage due to its minimal quantity.

As used herein, "magnetic coercivity", also known as coercive field or coercive force, refers to a measure of the ability of a ferromagnetic material to withstand an external magnetic field without becoming demagnetized. Coercivity is usually measured in oersted or ampere/meter units and is denoted $H_C$. A low coercivity means the nanoparticles can easily be manipulated to reverse their magnetic moments in response to an alternating magnetic field. A low coercivity is desired in magnetic hyperthermia treatment for optimal heating efficiency because it allows the nanoparticles to readily flip their magnetic moments in response to an alternating magnetic field, generating heat through hysteresis losses.

Aspects of the present disclosure are directed to a method of treating cancer using superparamagnetic iron oxide nanoparticles encapsulated within melanin derived from *Nigella sativa* through magnetic hyperthermia. Magnetic hyperthermia has been introduced clinically as an alternative approach for the focal treatment of tumors. MH utilizes the heat generated by the magnetic nanoparticles (MNPs) when subjected to an alternating magnetic field (AMF). For magnetic hyperthermia treatment, a suitable target temperature range is typically considered to be between 42 and 45° C., which heats the tumor tissue to a level that damages cancer cells while minimizing harm to surrounding healthy tissues. Unlike conventional MNPs, which struggle with heating efficiency and safety, the present Mel-MNPs can swiftly reach temperatures of 42° C. or more, leading to the rapid destruction of cancer cells. Thus, the Mel-MNPs serve as a potent agent in enhancing the effectiveness of magnetic hyperthermia cancer treatments.

A method of treating cancer with magnetic hyperthermia therapy is described. Magnetic hyperthermia therapy is a medical treatment that uses high temperatures to damage and kill cancer cells, or to make them more susceptible to radiation or chemotherapy. The treatment works by delivering MNPs to a tumor, then heating the MNPs with an alternating magnetic field to enable the MNPs to generate heat that damages the surrounding cancer cells. FIG. 1 illustrates a schematic flow chart of a method 50 of treating cancer with magnetic hyperthermia therapy. The order in which the method 50 is described is not intended to be construed as a limitation, and any number of the described method steps can be combined to implement the method 50. Additionally, individual steps may be removed or skipped from the method 50 without departing from the spirit and scope of the present disclosure.

At step 52, the method 50 comprises heating an aqueous metal chloride mixture to a temperature of 60° C. to 100° C. and reacting the aqueous metal chloride mixture with an ammonia hydroxide solution to obtain metal oxide nanoparticles. In one embodiment, a metal chloride is dissolved in water to form the aqueous metal chloride mixture. In some embodiments, the metal chloride is at least one selected from $FeCl_3$, $FeCl_2$, $CoCl_2$, $KCl$, $NH_4Cl$, $MgCl_2$, $NaCl$, $BrCl_2$, $CaCl_2$, $NiCl_2$, and $SrCl_2$. In another embodiment, the metal chloride is at least one selected from the group consisting of $FeCl_3$ and $FeCl_2$. In one embodiment, the metal chloride is a metal chloride hydrate. In some embodiments, the metal chloride is at least one selected from the group consisting of $CoCl_2 \cdot 2H_2O$, $CoCl_2 \cdot 6H_2O$, $NH_4Cl \cdot H_2O$, $NH_4Cl \cdot 2H_2O$, $MgCl_2 \cdot 6H_2O$, $MgCl_2 \cdot 2H_2O$, $BrCl_2 \cdot 2H_2O$, $CaCl_2 \cdot 2H_2O$, $CaCl_2 \cdot 6H_2O$, $NiCl_2 \cdot 6H_2O$, $SrCl_2 \cdot 6H_2O$, $FeCl_2 \cdot 4H_2O$, and $FeCl_3 \cdot 6H_2O$. In a preferred embodiment, the metal chloride is at least one selected from the group consisting of $FeCl_2 \cdot 4H_2O$ and $FeCl_3 \cdot 6H_2O$. In one embodiment, the aqueous metal chloride mixture has a weight ratio of $FeCl_2 \cdot 4H_2O$ to $FeCl_3 \cdot 6H_2O$ of 1:10 to 1:1. In another embodiment, the aqueous metal chloride mixture has a weight ratio of $FeCl_2 \cdot 4H_2O$ to $FeCl_3 \cdot 6H_2O$ of 1:9 to 1:2, preferably 1:8 to 1:2, preferably 1:7 to 1:2, preferably 1:6 to 1:2, preferably 1:5 to 1:2, preferably 1:4 to 1:2, preferably 1:3 to 1:2, most preferably 1:2.74. In a preferred embodiment, the aqueous metal chloride mixture has a weight ratio of $FeCl_2 \cdot 4H_2O$ to $FeCl_3 \cdot 6H_2O$ of about 1:2.74.

In one embodiment, the aqueous metal chloride mixture is heated to a temperature of 60 to 100° C., preferably 62 to 98° C., preferably 64 to 96° C., preferably 66 to 94° C., preferably 68 to 92° C., preferably 70 to 90° C., preferably 72 to 88° C., preferably 74 to 86° C., preferably 76 to 84° C., preferably 78 to 82° C., preferably 80 to 82° C., most preferably 80° C. to ensure complete dissolution of the metal chloride is water. In some embodiments, the aqueous metal chloride mixture is stirred while heating to ensure dissolution and to avoid uneven nucleation and aggregation of particles. In another embodiment, the aqueous metal chloride mixture is stirred at a rate of 500 to 1200 rpm, preferably 550 to 1150 rpm, preferably 600 to 1100 rpm, preferably 650 to 1050 rpm, preferably 700 to 1000 rpm, preferably 750 to 950 rpm, preferably 800 to 900 rpm, most preferably 800 to 850 rpm.

In some embodiments, an ammonium hydroxide solution is added to the aqueous metal chloride mixture. In one embodiment, the concentration of ammonium hydroxide in the ammonium hydroxide is at least 15%, preferably at least 16%, preferably at least 17%, preferably at least 18%, preferably at least 19%, preferably at least 20%, preferably at least 21%, preferably at least 22%, preferably at least 23%, preferably at least 24%, most preferably at least 25%. In one embodiment, the aqueous metal chloride mixture is maintained at a temperature of 80° C. and continuously stirred at a rate of 800 to 850 rpm for 10 to 35 min, preferably 11 to 34 min, preferably 12 to 33 min, preferably 13 to 32 min, preferably 14 to 31 min, preferably 15 to 30 min, preferably 16 to 30 min, preferably 17 to 30 min, preferably 18 to 30 min, preferably 19 to 30 min, preferably 20 to 30 min, preferably 21 to 30 min, preferably 22 to 30 min, preferably 23 to 30 min, preferably 24 to 30 min, preferably 25 to 30 min, preferably 26 to 30 min, preferably 27 to 30 min, preferably 28 to 30 min, preferably 29 to 30 min, most preferably 30 min. Addition the ammonium hydroxide solution causes the metal chlorides to react with the ammonium hydroxide to produce metal hydroxides. The metal hydroxides are then subsequently decomposed to form metal oxides and water vapor. In some embodiments, the addition of the ammonium hydroxide solution and the heating of the aqueous chloride mixture forms a solid precipitate. The precipitate may be further washed with a solvent, and further dried in an inert atmosphere, preferably under vacuum, to prevent any further chemical reactions from occurring. Suitable solvents include, but are not limited to, deionized water, distilled water, heavy water, hard water, feed water, and the like. Washing the precipitate with water as the solvent allows the metal oxide nanoparticles to remain functional and stable, which aids in preventing aggregation of the nanoparticles. In a preferred embodiment, the precipitate is washed with distilled water and dried for 16 to 32 h, preferably 18 to 30 h, preferably 20 to 28 h, preferably 22 to 26 h, most preferably 24 h, to obtain metal oxide nanoparticles. In a preferred embodiment, the metal nanoparticles are iron oxide nanoparticles.

At step 54, the method comprises obtaining *Nigella sativa*-derived melanin. *Nigella sativa*-derived melanin is obtained from the seedcoat of *Nigella sativa*. *Nigella sativa* (also known as black cumin) is an annual flowering plant in the family Ranunculaceae, native to eastern Europe and western Asia. *Nigella sativa* seeds comprise melanin, which is a dark pigment that may be extracted from the seed coat. The melanin extracted from *Nigella sativa* seed coats may exhibit strong free radical scavenging abilities, which enhances stability and reactivity in magnetic hyperthermia applications. Specifically, melanin may provide beneficial effects in magnetic hyperthermia applications because melanin has strong light absorption capabilities (i.e., ability to generate heat when exposed to light), potentially enhancing the heating effect desired when exposed to alternating magnetic fields during magnetic hyperthermia applications. Compared to melanin from other sources, melanin obtained from *Nigella sativa* may allow for more targeted cellular interactions due to its potent anti-inflammatory properties and high antioxidant levels. Melanin obtained from *Nigella sativa* has a higher electron spin density, an indicator of its potent antioxidant capacity, allowing it to effectively neutralize reactive oxygen species (ROS) and reactive nitrogen species (RNS) involved in cancer progression. Its antioxidant activity also helps protect cells from oxidative stress, a key factor in DNA mutations that may lead to cancer. Thus, melanin obtained from *Nigella sativa* may provide synergistic effects to the iron oxide nanoparticles allowing for more efficient and targeted magnetic hyperthermia treatment. The method of obtaining *Nigella sativa*-derived melanin comprises breaking down the black seed coats of *Nigella sativa* and extracting melanin, which is typically bound within the seed coat structure. In some embodiments, the method comprises solubilizing black seed coats of *Nigella sativa* in a NaOH solution for at least 1 h, preferably at least 1.5 h, preferably at least 2 h, preferably at least 2.5 h, preferably at least 3 h, preferably at least 3.5 h, most preferably at least 4 h, to obtain an extract solution. In some embodiments, the pH of the NaOH solution is 10 to 14, preferably 10.5 to 13.5, preferably 11 to 13, preferably 11.5 to 12.5, preferably 12 to 12.5, most preferably 12.5. In some embodiments, the molar concentration of the NaOH solution is 0.001 to 0.01 M, preferably 0.002 to 0.009 M, preferably 0.003 to 0.008 M, preferably 0.003 to 0.007 M, preferably 0.003 to 0.006 M, preferably 0.003 to 0.005 M, preferably 0.003 to 0.004 M, most preferably 0.0316 M. In other embodiments, strong bases such as alkali metal hydroxides (e.g., KOH, LiOH, RbOH, and CsOH) or alkaline earth metal hydroxides (e.g., $Ca(OH)_2$, $Sr(OH)_2$, and $Br(OH)_2$) may be used in place of the NaOH solution. In some embodiments, the *Nigella sativa* black seed coats are solubilized in the NaOH solution at a temperature of 20 to 35° C., although higher temperatures in the range of 40 to 50° C. may also enhance the degradation or solubilization process. Temperatures beyond 50° C. are not preferred, as it may cause degradation of melanin.

In one embodiment, the extract solution comprises melanin and other soluble components from the seedcoat. In one embodiment, the extract solution is centrifuged at a rate of 1000 to 4000 rpm for 1 to 10 min to obtain a solid residue and a supernatant. In some embodiments, the extract solution is centrifuged at a rate of 1200 to 4000 rpm, preferably 1400 to 4000 rpm, preferably 1600 to 4000 rpm, preferably 1800 to 4000, preferably 2000 to 4000 rpm, preferably 2200 to 4000 rpm, preferably 2400 to 4000 rpm, preferably 2600 to 4000, preferably 2800 to 4000 rpm, preferably 3000 to 4000 rpm, preferably 3200 to 4000 rpm, preferably 3400 to 4000, preferably 3600 to 4000 rpm, preferably 3800 to 4000 rpm, most preferably 4000 rpm. In some embodiments, the extract solution is centrifuged at a rate of 1000 to 4000 rpm for 2 to 9 min, preferably 3 to 8 min, preferably 4 to 7 min, preferably 5 to 6 min, most preferably 5 min to obtain a solid residue and a supernatant. In a preferred embodiment, the extract solution is centrifuged at a rate of 4000 rpm for 5 min to obtain a solid residue and a supernatant.

Melanin extracted from *Nigella sativa* seeds is primarily comprised of a mixture of polyphenolic compounds, such as thymoquinone, thymohydroquinone, dithymoquinone, thymol, and carvacrol. These are considered the main bioactive components responsible for the melanin-like properties observed in *Nigella sativa* seed coat extracts. In some embodiments, *Nigella sativa* seed coat extract comprises 30 to 50 wt. % of thymoquinone relative to a total weight of the extract, preferably 30 to 49 wt. %, most preferably 30 to 48 wt. %. In other embodiments, the *Nigella sativa* seed coat extract comprises thymohydroquinone, dithymoquinone, carvacrol, and thymol in an amount of 20 wt. % or less relative to a total weight of the extract. In one embodiment, the *Nigella sativa* seed coat extract comprises thymohydroquinone in an amount of 20 wt. % or less, preferably 19 wt. % or less, preferably 18 wt. % or less, preferably 17 wt. % or less, preferably 16 wt. % or less, most preferably 15 wt. % or less. In one embodiment, the *Nigella sativa* seed coat extract comprises dithymoquinone in an amount of 20 wt. % or less, preferably 19 wt. % or less, preferably 18 wt. % or less, preferably 17 wt. % or less, preferably 16 wt. % or less, preferably 15 wt. % or less, preferably 14 wt. % or less, preferably 13 wt. % or less, preferably 12 wt. % or less, most preferably 11 wt. % or less. In one embodiment, the *Nigella sativa* seed coat extract comprises carvacrol in an amount of 12 wt. % or less, preferably 11 wt. % or less, preferably 10 wt. % or less, preferably 9 wt. % or less, preferably 8 wt. % or less, most preferably 7 wt. % or less. In one embodiment, the *Nigella sativa* seed coat extract comprises thymol in an amount of 10 wt. % or less, preferably 9 wt. % or less, preferably 8 wt. % or less, preferably 7 wt. % or less, preferably 6 wt. % or less, most preferably 5 wt. % or less. The *Nigella sativa* seed coat extract may further comprise other compounds in trace amounts such as, but not limited to, isoquinoline alkaloids (e.g., nigellicimine and nigellicimine-N-oxide), pyrazol alkaloids (e.g., nigellidine and nigellicine), alpha-hederin, carvone, limonene, citronellol, various vitamins and minerals such as copper, phosphorus, zinc, iron, and the like, unsaturated fatty acids (e.g., linoleic acid, oleic acid, eicodadienoic acid, and dihomolinoleic acid), and saturated fatty acids (e.g., palmitic and stearic acid).

In some embodiments, a HCl solution is added to the solid residue to obtain a precipitate comprising melanin. In another embodiment, a strong mineral acid solution such as a nitric acid solution or a sulfuric acid solution may also be used in place of the HCl solution. In one embodiment, the HCl solution has a pH of 1 to 4, preferably 1.5 to 3.5, preferably 2 to 3, preferably 2 to 2.5, most preferably 2. In another embodiment, the HCl solution has a molar concentration of 0.001 to 0.01 M, preferably 0.002 to 0.01 M, preferably 0.003 to 0.01 M, preferably 0.004 to 0.01 M, preferably 0.005 to 0.01 M, preferably 0.006 to 0.01 M, preferably 0.007 to 0.01 M, preferably 0.008 to 0.01 M, preferably 0.008 to 0.01 M, preferably 0.009 to 0.01 M, most preferably 0.01 M. In some embodiments, the addition of the HCl solution to the solid residue is repeated several times to obtain a melanin precipitate with increased purity. In some embodiments, the addition of the HCl solution to the solid residue is repeated 1 to 5 times, preferably 2 to 4 times, preferably 2 to 3 times, most preferably 2 times. In some embodiments, the melanin precipitate is further filtered, washed, and dried to obtain the *Nigella sativa*-derived melanin. In one embodiment, the melanin precipitate is dried at a temperature of 60 to 90° C. for 1 to 24 h. In some embodiments, the melanin precipitate is dried at a temperature of 65 to 85° C., preferably 70 to 80° C., preferably 75 to 80° C., most preferably 80° C. In another embodiment, the melanin precipitate is dried for 2 to 22 h, preferably 4 to 20 h, preferably 6 to 18 h, preferably 8 to 16 h, preferably 8 to 14 h, most preferably 8 to 12 h.

At step 56, the method 50 comprises sonicating a buffered aqueous suspension of the metal oxide nanoparticles and the *Nigella sativa*-derived melanin to obtain melanin-coated magnetite nanoparticles (Mel-MNPs). In one embodiment, the buffered aqueous suspension comprises at least one selected from (4-(2-hydroxyethyl)-1-piperazineethanesulfonic acid (HEPES), 3-(N-morpholino)propanesulfonic acid (MOPS), and tris(hydroxymethyl)aminomethane hydrochloride (Tris-HCl). In a preferred embodiment, the buffered aqueous solution comprises Tris-HCl. In some embodiments, the molar concentration of Tris-HCl in the buffered aqueous solution is about 5 to 15 mM, preferably 6 to 14 mM, preferably 7 to 13 mM, preferably 8 to 12 mM, preferably 9 to 11 mM, preferably 10 mM. In one embodiment, the pH of the Tris-HCl in the buffered aqueous solution is 6 to 10, preferably 7 to 9, preferably 8 to 9, more preferably at about 8.5.

In some embodiments, the weight ratio of the metal oxide nanoparticles to *Nigella sativa*-derived melanin in the buffered aqueous suspension is about 1:15 to 15:1, preferably 1:14 to 14:1, preferably 1:13 to 13:1, preferably 1:12 to 12:1, preferably 1:11 to 11:1, preferably 1:10 to 10:1, preferably 1:9 to 10:1, preferably 1:8 to 10:1, preferably 1:7 to 10:1, preferably 1:6 to 10:1, preferably 1:5 to 10:1, preferably 1:4 to 10:1, preferably 1:3 to 10:1, preferably 1:2 to 10:1, preferably 1:1 to 10:1, preferably 2:1 to 10:1, preferably 3:1 to 10:1, preferably 4:1 to 10:1, preferably 5:1 to 10:1, preferably 6:1 to 10:1, preferably 7:1 to 10:1, preferably 8:1 to 10:1, preferably 9:1 to 10:1, most preferably 10:1. In some embodiments, the buffered aqueous suspension is sonicated for 10 to 40 min at a frequency of 15 to 50 kHz to obtain the Mel-MNPs. In other embodiments, the buffered aqueous suspension is sonicated for 15 to 35 min, preferably 20 to 30 min, preferably 25 to 30 min, most preferably 30 min. In other embodiments, the buffered aqueous suspension is sonicated for at a frequency of 20 to 45 kHz, preferably 20 to 40 kHz, preferably 20 to 35 kHz, preferably 20 to 30 kHz, preferably 20 to 25 kHz, most preferably 20 kHz.

In an embodiment, the Mel-MNPs demonstrate a core-shell morphology, meaning that the Mel-MNPs comprise a core and a shell encompassing said shell. In one embodiment, the Mel-MNPs have a core comprising of the magnetic iron oxide nanoparticles and a shell comprising melanin encompassing the magnetic iron oxide nanoparticles. In some embodiments, the Mel-MNPs have an average particle diameter of 20 nm or less, preferably 19.5 nm or less, preferably 19 nm or less, preferably 18.5 nm or less, preferably 18 nm or less, preferably 17.5 nm or less, preferably 17 nm or less, preferably 16.5 nm or less, preferably 16 nm or less, preferably 15.5 nm or less, preferably 15 nm or less, preferably 14.5 nm or less, preferably 14 nm or less, preferably 13.5 nm or less, preferably 13 nm or less, preferably 12.5 nm or less, preferably 12 nm or less, most preferably 11.69 nm. The D90 is the particle diameter at which 90% of the particles are smaller and 10% are larger, while the D10 is the particle diameter at which 10% of the particles are smaller and 90% are larger. In one embodiment, the D90 of the Mel-MNPs is 25 nm or less, preferably 24 nm or less, preferably 23 nm or less, preferably 22 nm or less, preferably 21 nm or less, preferably 20 nm or less, preferably 19 nm or less, preferably 18 nm or less, preferably 17 nm or less, preferably 16 nm or less, preferably 15 nm or less, most preferably 14 nm or less. In one embodiment, the D10 of the Mel-MNPs is 14 nm or less, preferably 13 nm or less, preferably 12 nm or less, preferably 11 nm or less, preferably 10 nm or less, preferably 9 nm or less, preferably 8 nm or less, most preferably 7 nm or less.

At step 58, the method 50 comprises contacting the Mel-MNPs with the cancer. As used herein, the term 'cancer' refers to all types of cancer, neoplasm, or malignant tumors found in mammals (e.g., humans), including leukemias, lymphomas, carcinomas, and sarcomas. Exemplary cancers that may be treated with a compound or method provided herein include, but are not limited to, brain cancer, glioma, glioblastoma, neuroblastoma, prostate cancer, colorectal cancer, pancreatic cancer, Medulloblastoma, melanoma, cervical cancer, gastric cancer, ovarian cancer, lung cancer, cancer of the head, Hodgkin's Disease, and Non-Hodgkin's Lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumor, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer. In an embodiment, the cancer is a breast cancer. In a preferred embodiment, the breast cancer is at least one cancer cell line selected from the group consisting of MDAMB231 and KAIMRC1. In one embodiment, the cancer is the cell line MDAMB231. In another embodiment, the cancer is the cell line KAIMRC1. In one embodiment, the method of contacting the cancer cells comprises administering a composition comprising the Mel-MNPs in a concentration of at least 1 mg/mL, preferably at least 2 mg/mL, preferably at least 3 mg/mL, preferably at least 4 mg/mL, preferably at least 5 mg/mL, preferably at least 6 mg/mL, preferably at least 7 mg/mL, preferably at least 8 mg/mL, preferably at least 9 mg/mL, most preferably at least 10 mg/mL to the cancer.

At step 60, the method 50 comprises applying an external alternating magnetic field to the Mel-MNPs to generate heat and to hyperthermically treat the cancer. When exposed to the external alternating magnetic field, the Mel-MNPs heat up by converting electromagnetic energy into heat through processes, such as hysteresis loss, Néel relaxation, and Brownian relaxation. In magnetic hyperthermia, hysteresis loss occurs when magnetic nanoparticles are exposed to an alternating magnetic field, causing their magnetization to repeatedly reverse direction, which generates heat due to the internal friction within the particles as they try to align with the changing field. Similarly, Néel relaxation occurs when the magnetic moment within a single-domain magnetic nanoparticle rapidly flips direction to align with an applied alternating magnetic field, generating heat due to internal friction within the particle itself, while the particle remains stationary in the surrounding fluid. Brownian relaxation refers to the heating process generated when magnetic nanoparticles physically rotate within a fluid due to the alternating magnetic field, essentially causing friction and dissipating heat as the particles try to align their magnetic moments with the changing field direction. This rotation is influenced by the viscosity of the medium, with higher viscosity leading to less Brownian relaxation and less heat generation. In one embodiment, the composition comprising the Mel-MNPs has a viscosity of 1 to 20 mPas, preferably 1 to 19 mPas, preferably 1 to 18 mPas, preferably 1 to 17 mPas, preferably 1 to 16 mPas, preferably 1 to 15 mPas, preferably 1 to 14 mPas, preferably 1 to 13 mPas, preferably 1 to 12 mPas, preferably 1 to 11 mPas, preferably 1 to 10 mPas, preferably 1 to 9 mPas, most preferably 1 to 8 mPas.

The amount of heat generated depends on the frequency and amplitude of the alternating magnetic field. In some embodiments, applying the external alternating magnetic field to the Mel-MNPs in the cancer cell line achieves an internal temperature of the cancer of at least 45° C. in 12 min or less at a frequency of 300 to 700 kHz and an amplitude of 100 to 200 Oe. In one embodiment, the external alternating magnetic field has a frequency of 305 to 695 kHz, preferably 310 to 690 kHz, preferably 315 to 685 kHz, preferably 320 to 680 kHz, preferably 325 to 675 kHz, preferably 330 to 670 kHz, preferably 330 to 665 kHz, preferably 330 to 660 kHz, preferably 330 to 655 kHz, preferably 330 to 650 kHz, preferably 330 to 645 kHz, preferably 330 to 640 kHz, preferably 330 to 635 kHz, most preferably 330 to 630 kHz. In one embodiment, the application of the external magnetic field to the Mel-MNPs in the cancer cell line achieves an internal temperature of the cancer of at least 45° C., preferably at least 46° C., preferably 47° C., preferably at least 48° C., preferably at least 49° C., preferably at least 50° C., preferably at least 51° C., preferably at least 52° C., preferably at least 53° C., preferably at least 54° C., preferably 55° C., preferably at least 56° C., preferably at least 57° C., preferably at least 58° C., preferably at least 59° C., preferably at least 60° C., preferably at least 61° C., preferably at least 62° C. In another embodiment, the application of the external magnetic field to the Mel-MNPs in the cancer line achieves an internal temperature of the cancer of at least 45° C. in 12 min or less, preferably 11 min or less, preferably 10 min or less, preferably 9 min or less, preferably 8 min or less, preferably 7 min or less, preferably 6 min or less, preferably 5 min or less, most preferably 4 min or less. In yet another embodiment, the application of the external magnetic field to the Mel-MNPs in the cancer line achieves an internal temperature of the cancer of at least 45° C. in 12 min or less at an amplitude of 100 to 200 Oe, preferably 105 to 195 Oe, preferably 110 to 190 Oe, preferably 115 to 180 Oe, preferably 120 to 175 Oe, preferably 120 to 170 Oe, preferably 120 to 165 Oe, most preferably 120 to 160 Oe. Increasing the frequency of the alternating magnetic field directly increases the amount of heat generated by magnetic nanoparticles, meaning higher frequencies lead to more efficient heating due to the increased rate of magnetization reversal within the nanoparticles. Similarly, a higher field amplitude directly affects the amount of heat generated by magnetic nanoparticles because the stronger the magnetic field, the more the nanoparticles will rotate and generate heat due to their magnetic properties.

In some embodiments, the Mel-MNPs have a remanence of 0.05 to 1 emu/g. A "low remanence" refers to a material with a relatively weak residual magnetic field, meaning it retains very little magnetism after an external magnetic field is removed; in simpler terms, it is a material that loses its magnetism easily and has a low magnetic strength when no external field is applied. A "high remanence" refers to a material that retains a significant amount of magnetization even after the external magnetic field is removed, meaning it has a strong residual magnetism. Remanence may be affected by the particle size of the nanoparticles. Smaller particles allow thermal fluctuations to easily flip the magnetic moment, leading to low remanence values. In magnetic hyperthermia applications, low remanence is preferred. MNPs with low remanence ensures that the nanoparticles readily respond to the alternating magnetic field, maximizing heat generation. Additionally, with low remanence there is less residual magnetism such that there is less risk of magnetic particle aggregation or unwanted interactions with surrounding tissues once the magnetic field is turned off. In some embodiments, the Mel-MNPs have a remanence of 0.06 to 0.95 emu/g, preferably 0.065 to 0.90 emu/g, preferably 0.07 to 0.85 emu/g, preferably 0.075 to 0.80 emu/g, preferably 0.08 to 0.75 emu/g, preferably 0.085 to 0.70 emu/g, preferably 0.085 to 0.65 emu/g, preferably 0.085 to 0.60 emu/g, preferably 0.085 to 1.05 emu/g, preferably 0.085 to 1.00 emu/g, preferably 0.085 to 0.95 emu/g, preferably 0.085 to 0.90 emu/g, preferably 0.085 to 0.85 emu/g, preferably 0.085 to 0.80 emu/g, preferably 0.085 to 0.75 emu/g, preferably 0.085 to 0.70 emu/g, preferably 0.085 to 0.65 emu/g, preferably 0.085 to 0.60 emu/g, preferably 0.085 to 0.55 emu/g, preferably 0.085 to 0.50 emu/g, preferably 0.085 to 0.45 emu/g, preferably 0.085 to 0.40 emu/g, preferably 0.085 to 0.35 emu/g, preferably 0.085 to 0.30 emu/g, preferably 0.085 to 0.25 emu/g, preferably 0.085 to 0.20 emu/g, preferably 0.085 to 0.15 emu/g, preferably 0.085 to 0.10 emu/g, preferably 0.085 to 0.095 emu/g, preferably 0.085 to 0.09 emu/g, most preferably 0.087 emu/g.

In some embodiments, the Mel-MNPs have a magnetic coercivity ($H_C$) of 4.5 to 6.5 Oe. A material having a low magnetic coercivity means a material that easily loses its magnetization when exposed to a relatively weak external magnetic field. Thus, a material having a low magnetic coercivity is easily demagnetized. A material having a high magnetic coercivity means a material that has a strong resistance to losing its magnetism when exposed to an external magnetic field. Thus, a material having a high magnetic coercivity requires a high magnetic field strength to demagnetize it. The magnetic coercivity of MNPs may be affected by their particle size and shape, with smaller particles tending to have lower coercivity due to increased Brownian relaxation. MNPs with higher coercivity generally produce more heat in magnetic hyperthermia because they experience greater hysteresis losses when exposed to an alternating magnetic field. For effective magnetic hyperthermia, MNPs preferably have low coercivity so the MNPs can rapidly flip their magnetization when exposed to an alternating magnetic field, generating heat within the targeted tissue. When the MNPs have high coercivity, a large amount of energy is needed to switch their magnetization direction, which can lead to energy loss that is not converted into heat thus, leading to inefficient magnetic hyperthermia treatment. In another embodiment, the Mel-MNPs have a magnetic coercivity of 4.55 to 6.45 Oe, preferably 4.6 to 6.4 Oe, preferably 4.65 to 6.35, preferably 4.7 to 6.3 Oe, preferably 4.75 to 6.25 Oe, preferably 4.8 to 6.2 Oe, preferably 4.85 to 6.15, preferably 4.9 to 6.1 Oe, preferably 4.95 to 6.05 Oe, preferably 5 to 6 Oe, preferably 5.05 to 5.95, preferably 5.1 to 5.9 Oe, preferably 5.15 to 5.85 Oe, preferably 5.2 to 5.8 Oe, preferably 5.25 to 5.75, preferably 5.3 to 5.7 Oe, preferably 5.35 to 5.65 Oe, preferably 5.4 to 5.6 Oe, preferably 5.45 to 5.6 Oe, preferably 5.5 to 5.6 Oe, preferably 5.55 to 5.6, most preferably 5.586 Oe.

In some embodiments, the Mel-MNPs have a saturation magnetization ($M_s$) of 6.5 to 9 emu/g. Low saturation magnetization is a characteristic of materials that have a low maximum magnetization that can be induced by an external magnetic field. Contrastingly, high saturation magnetization is a characteristic of materials that can achieve a high level of magnetization when exposed to an external magnetic field. Materials with high saturation magnetization can absorb more energy from the alternating magnetic field, leading to greater heat production within the tumor tissue where the MNPs are located. Further, a higher saturation magnetization allows for the use of a lower concentration of nanoparticles to achieve the desired heating effect, potentially reducing toxicity concerns. In one embodiment, the Mel-MNPs have a saturation magnetization of 6.6 to 8.9 emu/g, preferably 6.7 to 8.8 emu/g, preferably 6.8 to 8.7 emu/g, preferably 6.9 to 8.6 emu/g, preferably 7 to 8.5 emu/g, preferably 7.1 to 8.4 emu/g, preferably 7.2 to 8.3 emu/g, preferably 7.3 to 8.2 emu/g, preferably 7.3 to 8.1 emu/g, preferably 7.3 to 8 emu/g, preferably 7.3 to 7.9 emu/g, preferably 7.3 to 7.8 emu/g, preferably 7.3 to 7.7 emu/g, preferably 7.3 to 7.6 emu/g, preferably 7.3 to 7.5 emu/g, preferably 7.3 to 7.4 emu/g, most preferably 7.371±0.01214 emu/g.

In some embodiments, the Mel-MNPs of the present disclosure have an $IC_{50}$ of 5 mg/mL or less against a cancer of at least one cancer cell line selected from the group consisting of MDAMB231 and KAIMRC2. In another embodiment, the Mel-MNPs have an $IC_{50}$ of 4.8 mg/mL or less, preferably 4.6 mg/mL or less, preferably 4.4 mg/mL or less, preferably 4.2 mg/mL or less, preferably 4 mg/mL or less, preferably 3.8 mg/mL or less, preferably 3.6 mg/mL or less, preferably 3.4 mg/mL or less, preferably 3.2 mg/mL or less, preferably 3 mg/mL or less, preferably 2.8 mg/mL or less, preferably 2.6 mg/mL or less, preferably 2.4 mg/mL or less, preferably 2.2 mg/mL or less, most preferably 2 mg/mL or less against at least one of MDAMB231 and KAIMRC2. In a specific embodiment, the Mel-MNPs have an $IC_{50}$ of 5 mg/mL or less, preferably 4.8 mg/mL or less, preferably 4.6 mg/mL or less, preferably 4.4 mg/mL or less, preferably 4.2 mg/mL or less, preferably 4 mg/mL or less, preferably 3.8 mg/mL or less, preferably 3.6 mg/mL or less, preferably 3.4 mg/mL or less, preferably 3.2 mg/mL or less, most preferably 3.156 mg/mL or less against MDAMB231. In a specific embodiment, the Mel-MNPs have an $IC_{50}$ of 4 mg/mL or less, preferably 3.8 mg/mL or less, preferably 3.6 mg/mL or less, preferably 3.4 mg/mL or less, preferably 3.2 mg/mL or less, preferably 3 mg/mL or less, preferably 2.8 mg/mL or less, preferably 2.6 mg/mL or less, preferably 2.4 mg/mL or less, preferably 2.2 mg/mL or less, most preferably 2.045 mg/mL or less against KAIMRC2. In another embodiment, a cell viability of the cancer is 90% or less when contacted with a composition comprising 0.01 to 20 mg/mL of Mel-MNPs. In one embodiment, a cell viability of the cancer is 90% or less, preferably 85% or less, preferably 80% or less, preferably 75% or less, preferably 70% or less, preferably 65% or less, preferably 60% or less, preferably 55% or less, preferably 50% or less, preferably 45% or less, preferably 40% or less, preferably 35% or less, preferably 30% or less, preferably 25% or less, most preferably 20% or less when contacted with a composition comprising 0.01 to 20 mg/mL of Mel-MNPs.

EXAMPLES

The following examples demonstrate a method of treating a cancer with magnetic hyperthermia therapy. The examples are provided solely for illustration and are not to be construed as limitations of the present disclosure, as many variations thereof are possible without departing from the spirit and scope of the present disclosure.

Example 1: Materials and Methods

Iron oxide nanoparticles were synthesized using the chemical co-precipitation technique, where multiple substances are mixed to form a solution and then a precipitant is added to the mixture to create solid particles. According to the present disclosure, 0.86 g of $FeCl_2 \cdot 4H_2O$ and 2.36 g of $FeCl_3 \cdot 6H_2O$ were mixed in distilled water under a nitrogen atmosphere. The obtained mixture was subjected to rigorous stirring and heated to about 80° C. Subsequently, 5 mL of a 25% $NH_4OH$ solution was gradually introduced. The mixture was maintained at 80° C. with continuous stirring for 30 min to facilitate full nanoparticle development. Further, the nanoparticles were repeatedly rinsed with distilled water and dried under vacuum for 24 hours. Natural melanin was then extracted from *Nigella sativa*. Black seed coats of *Nigella sativa* were solubilized in a solution of NaOH with a pH of about 12.5 for 4 hours, resulting in a dark brown solution. The dark brown solution was then filtered and centrifuged at 4000 rpm for 5 min. The melanin was precipitated from the solution using an HCl acid solution at pH 2. The aforementioned treatment was repeated twice to ensure an increased purity of the obtained melanin precipitate. The melanin precipitate was thoroughly washed four times with distilled water, filtered, and dried overnight at 80° C. to obtain a dry melanin powder. In order to synthesize the Mel-MNPs, 200 mg of the iron oxide nanoparticles were suspended in a buffered solution comprising 10 mL of 10 mM tris(hydroxymethyl)aminomethane hydrochloride (TRIS—HCl) buffer, at a pH of 8.5, and sonicated for 30 minutes. Subsequently, 20 mg of 2 mg/mL melanin was introduced into the mixture and stirred rigorously for 3 hours at room temperature. The Mel-MNPs were then thoroughly washed with deionized water and ethanol and dried in a vacuum oven.

Example 2: TEM and FTIR

Transmission electron microscopy (TEM) micrographs of the Mel-MNPs were obtained with an electron microscope Titan 300 kV ST (FEI). The TEM grids were plasma treated to remove dust and organic contaminants before imaging. A few drops of the sample were put to the grids for the imaging procedure, and they were left to dry under vacuum. An Agilent Cary 630 Fourier transform infrared (FTIR) spectrometer was used to collect the infrared spectral data. The FTIR spectrometer used a Michelson interferometer which operated in a wavenumber range of 400 $cm^{-1}$ to 4000 $cm^{-1}$. Magnetic characterization was performed at room temperature using a vibrating sample magnetometer (VSM, 7404 model) with 1.8 tesla (T) magnets. The heating efficiency was performed using a commercial system, Nanotherics MagneTherm.

Figure 2:
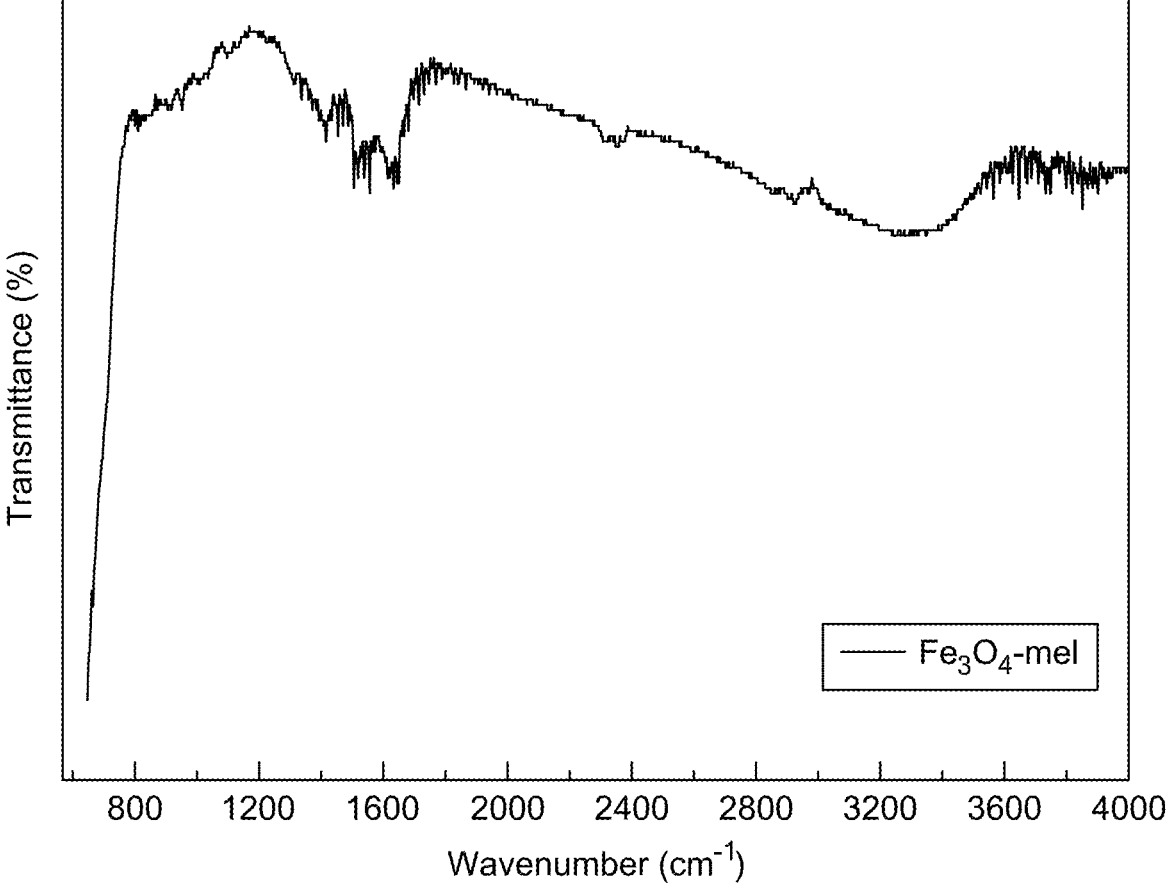
FIG. 2 is a graph depicting the Fourier transform infrared (FTIR) spectra of the iron-oxide and iron oxide nanoparticles coated with melanin (Mel-MNPs), according to certain embodiments.

According to the present disclosure, the FTIR spectra of synthesized magnetic nanoparticles, focusing on iron oxide nanoparticles coated with melanin (Mel-MNPs) was evaluated, as shown in FIG. 2. The FTIR spectra depicts characteristic peaks of iron oxide, such as a strong Fe—O stretching vibration around 580 $cm^{-1}$ and Fe—O—H bending vibrations between 1000 $cm^{-1}$ to 1500 $cm^{-1}$. In contrast, the red spectrum exhibits additional absorption bands indicative of melanin coating, including a broad O—H and N—H stretching peak around 3435 $cm^{-1}$, a C═O stretching peak at 1630 $cm^{-1}$, and aromatic C═C stretching vibrations between 1300 $cm^{-1}$ to 1450 $cm^{-1}$. The new bands confirm the presence of melanin on the iron oxide nanoparticles. The coating may enhance the applications of the Mel-MNPs in biomedical and environmental fields by combining the properties of the synthesized Mel-MNPs. The FTIR analysis thus validates the melanin coating process and underscores the importance of surface modification in improving the functionality of magnetic nanoparticles for advanced applications.

Figure 3A:
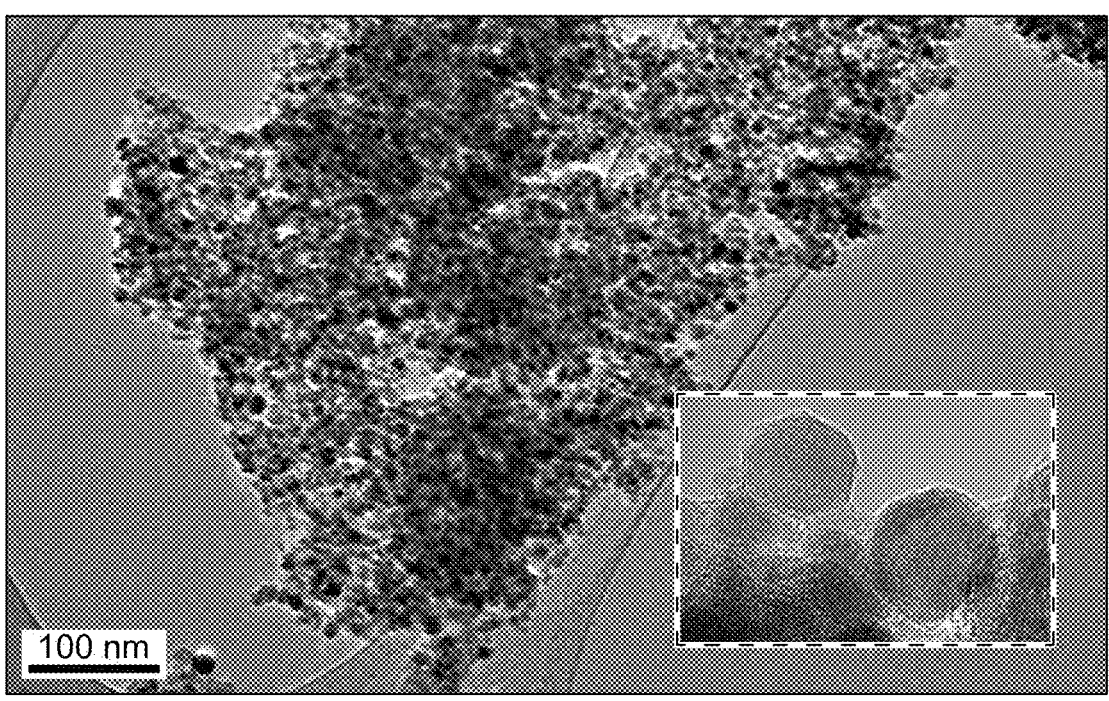
FIG. 3A is a transmission electron microscopy (TEM) micrograph of the Mel-MNPs, according to certain embodiments.
Figure 3B:
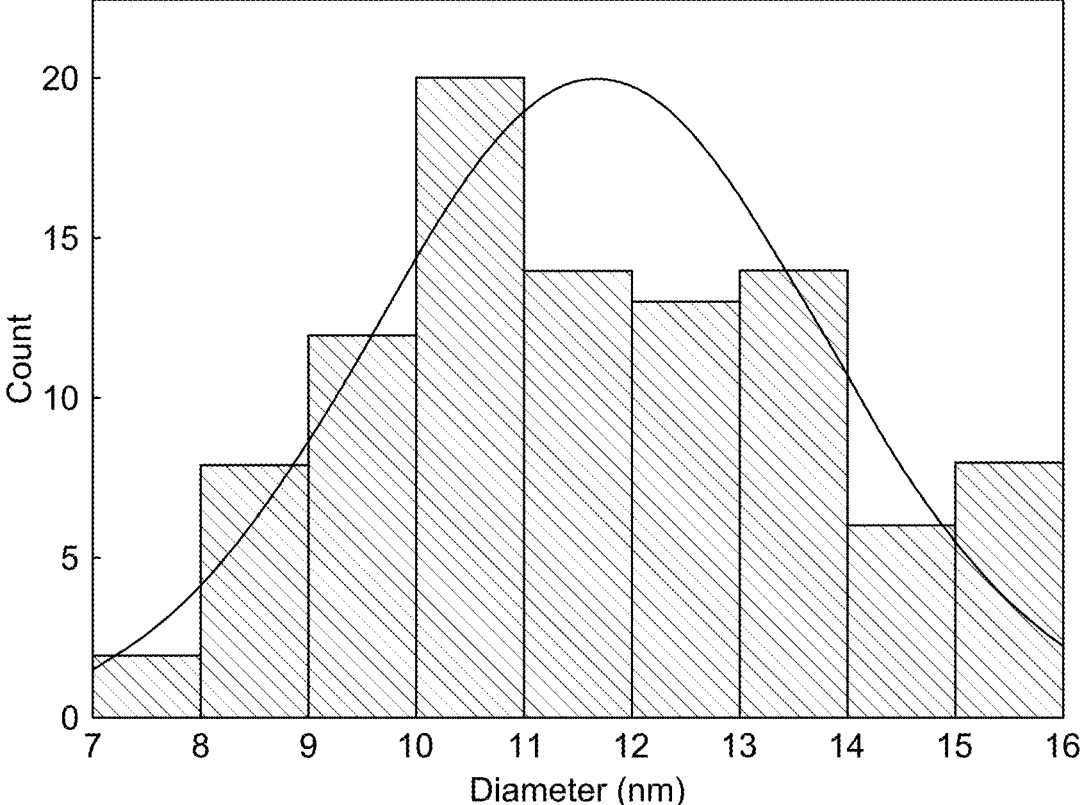
FIG. 3B is a particle size distribution (PSD) curve of the Mel-MNPs, according to certain embodiments.

Further, transmission electron microscopy (TEM) analysis was conducted. FIG. 3A shows the TEM images depicting Mel-MNPs, magnified to highlight structural characteristics of the Mel-MNPs. The Mel-MNPs exhibited a core-shell morphology, where the dense cores represent the magnetic iron oxide, and the diffuse outer layers indicate the melanin coating. The particle size diameters varied between 8 nm to 15 nm, illustrating a relatively uniform size distribution with a thin, consistent melanin shell. The particle size distribution was also determined from the TEM analysis using image analysis software to create a histogram showing the particle frequency at each diameter size, as shown in FIG. 3B. The average particle size is 11.69 nm for the Mel-MNPs. The crystalline nature of the iron oxide core is evidenced by the clear lattice fringes visible in the TEM images, indicating a high degree of crystallinity. The aforementioned structural configuration is preferred for applications that rely on the magnetic properties of the core and the biocompatible interfacing provided by the melanin shell, such as in targeted drug delivery or magnetic resonance imaging, because a high degree of crystallinity in magnetic particles allows for a more uniform alignment of magnetic moments within the particles, leading to stronger and more consistent magnetic properties. The TEM analysis corroborated the synthesis of the Mel-MNPs, showcasing the potential of Mel-MNPs in nanomedicine and other biomedical applications.

Example 3: Magnetic Characteristics of Mel-MNPs

Figure 4A:
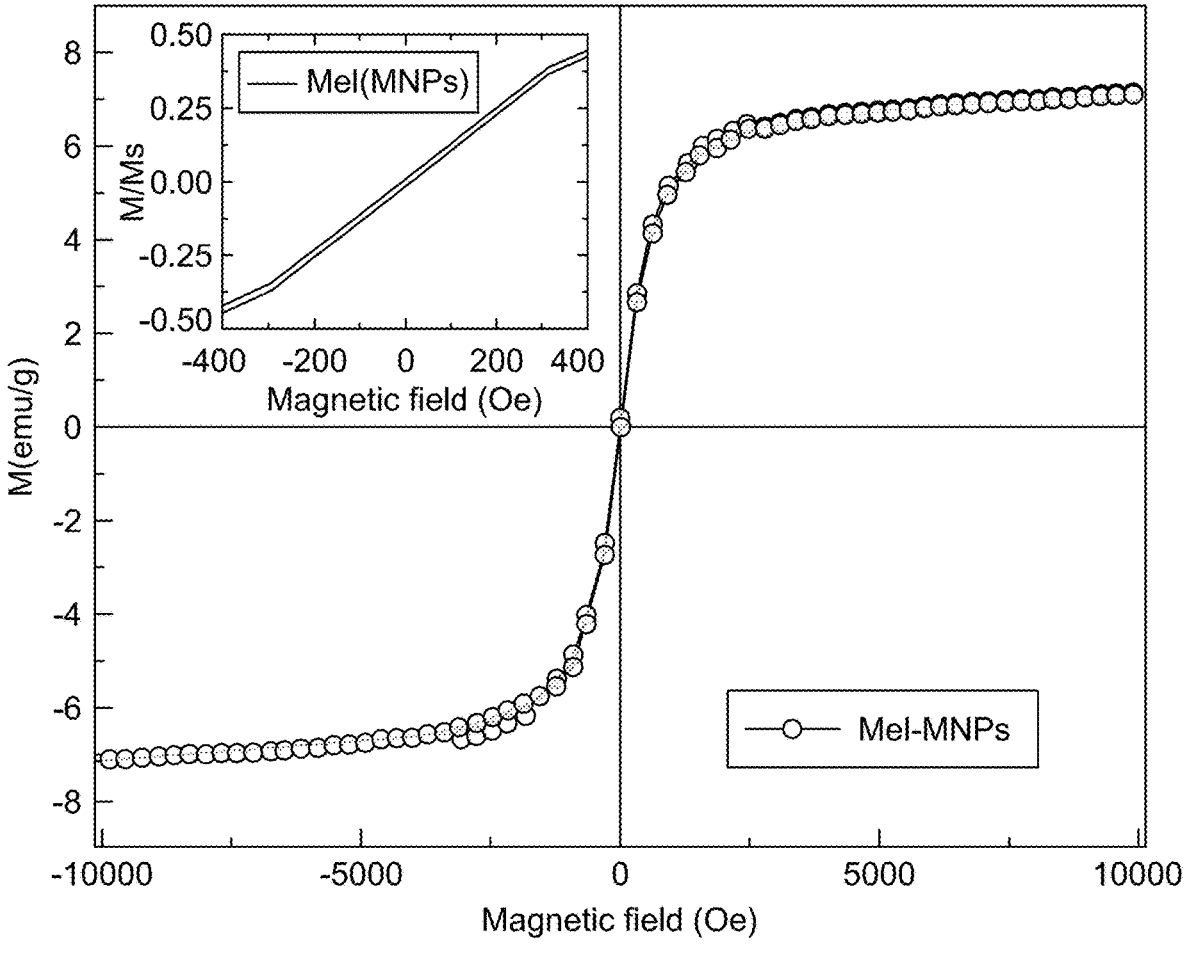
FIG. 4A is a magnetism (M-H) curve of the Mel-MNPs at 300 Kelvin (K), according to certain embodiments.
Figure 4B:
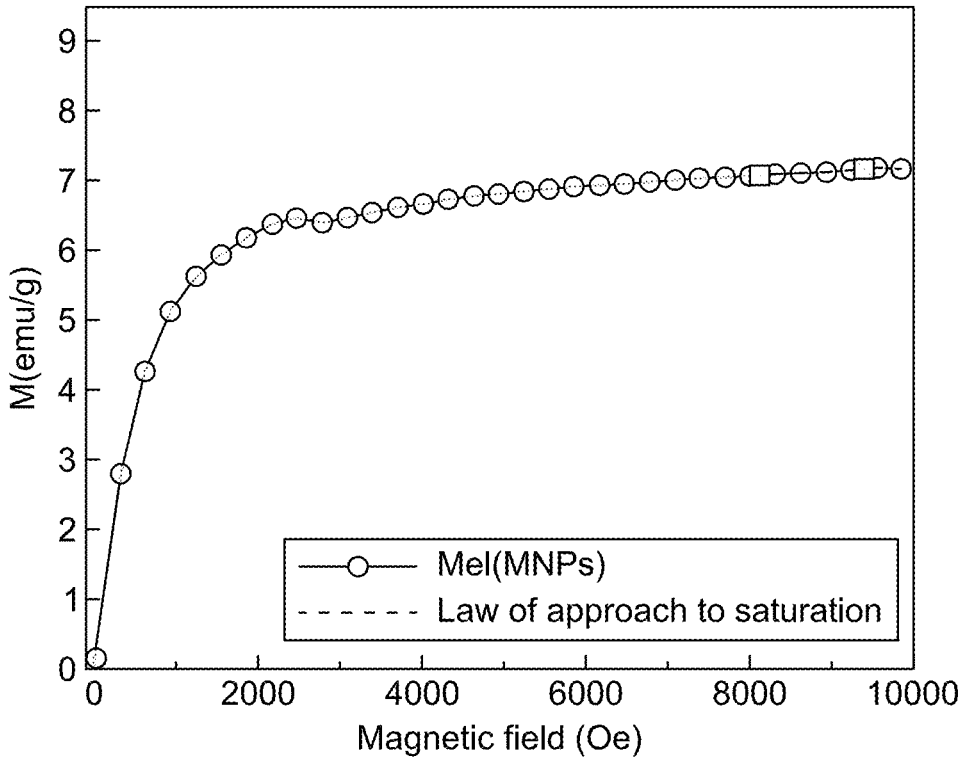
FIG. 4B is a graph depicting law of approach to saturation (LAS) curve for the Mel-MNPs, according to certain embodiments.

Referring to FIGS. 4A through 4B, magnetization curves as a function of applied magnetic field of the Mel-MNPs, collected at room temperature are illustrated. The coercivity ($H_C$) of Mel-MNPs was found to be 5.586 Oersted (Oe), and remanence is 0.087 emu/g. The considerable values of coercivity and remanence imply that the synthesized Mel-MNPs are superparamagnetic nanoparticles. It may be noted that the magnetization ($M_s$) after coated core shell is 7.176 emu/g. In order to confirm the saturation values and the effective anisotropy constant ($K_{eff}$), the following equation may be employed, using the law of approach to saturation (LAS), which explains the magnetization close to the saturation.

$$M(H) = M_s\left(1 - \frac{b}{H^2}\right)$$

Further, the following equation may be used to get the $K_{eff}$ using the parameter 'b'.

$$K_{eff} = \mu_0 M_s \sqrt{\frac{15b}{4}}$$

The calculated anisotropy values are listed in Table 1. It may be noted that the anisotropy constant is a vital parameter for defining the energy barrier for changing the direction of magnetization of a nanoparticle. In hyperthermia applications, the selection of an effective anisotropy constant whether high or low depends on the specific requirements and heating efficiency desired. The $M/M_s$-H curve illustrates the normalized magnetization (M) of a material in relation to its saturation magnetization ($M_s$) against the applied magnetic field (H). For superparamagnetic materials, the $M/M_s$-H curve shows a sharp increase in magnetization with rising applied field strength, eventually reaching a saturation point. A rising $M/M_s$-H curve indicates that the material responds more effectively to the applied magnetic field, leading to improved energy absorption and, consequently, more efficient and controlled heating of the targeted tissue.

TABLE 1

| | Magnetic properties calculated using a hysteresis loop and LAS fitting | | | | |
|---|---|---|---|---|---|
| MNPs sample | $M_s$ (emu/g) (Experimental) | $M_s$ (emu/g) (LAS fit) | $H_C$ (Oe) | $M_r$ (emu/g) | $K_{eff}$ (erg/cm³) |
| Mel-MNPs | 7.176 | 7.371 ± 0.01214 | 5.586 | 0.087 | 2.341 × 10⁴ |

Example 4: Heating Characteristics of Mel-MNPs

Figure 5A:
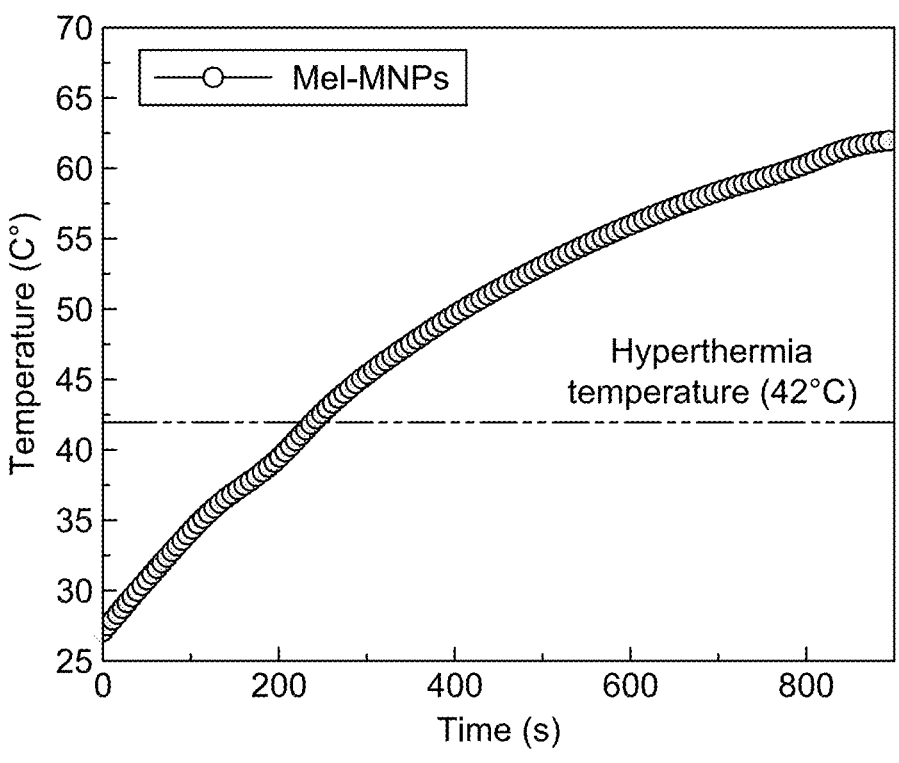
FIG. 5A is a graph depicting temperature rise for 10 mg/mL of Mel-MNPs, at a frequency of 332 kHz and field amplitude of 160 Oersted (Oe), according to certain embodiments.
Figure 5B:
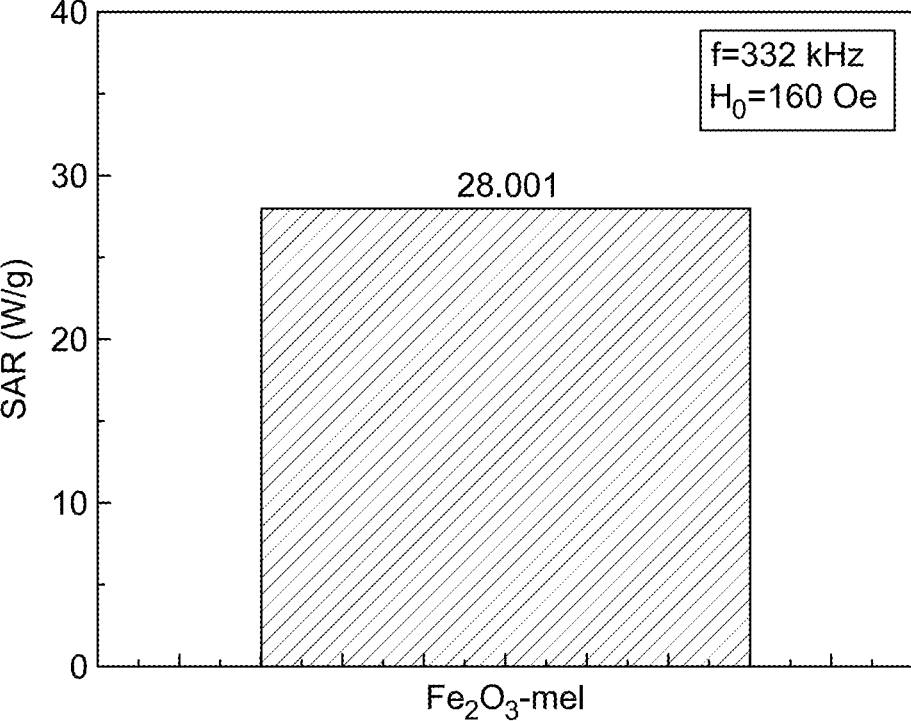
FIG. 5B is a graph depicting specific absorption rate (SAR) values of the Mel-MNPs, at a frequency of 332 kHz and field amplitude of 160 Oe, according to certain embodiments.
Figure 6A:
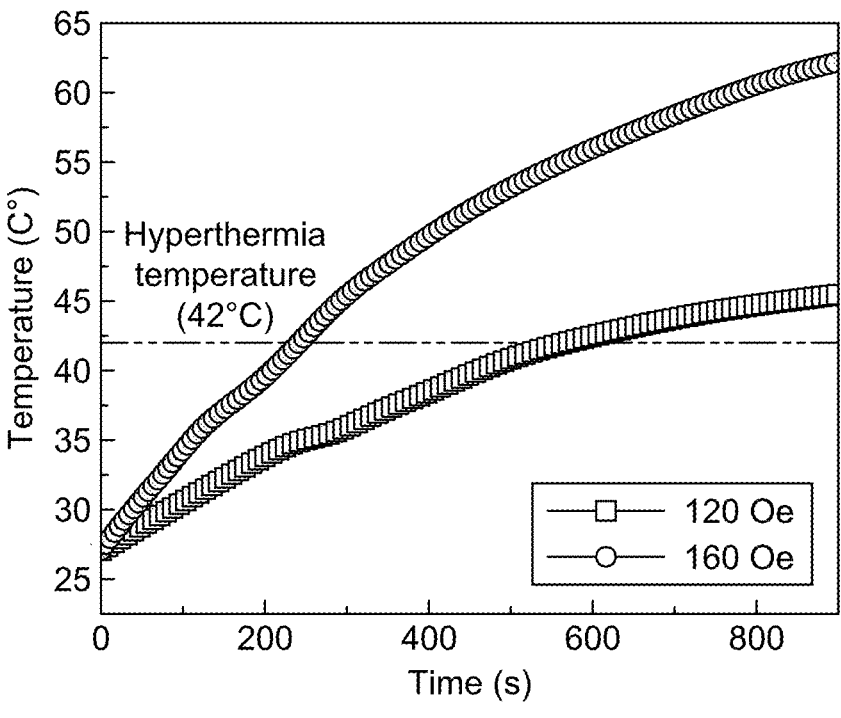
FIG. 6A is a graph depicting temperature rise at different field amplitude, a frequency of 332 kHz, a concentration of 10 mg/mL of the Mel-MNPs, according to certain embodiments.
Figure 6B:
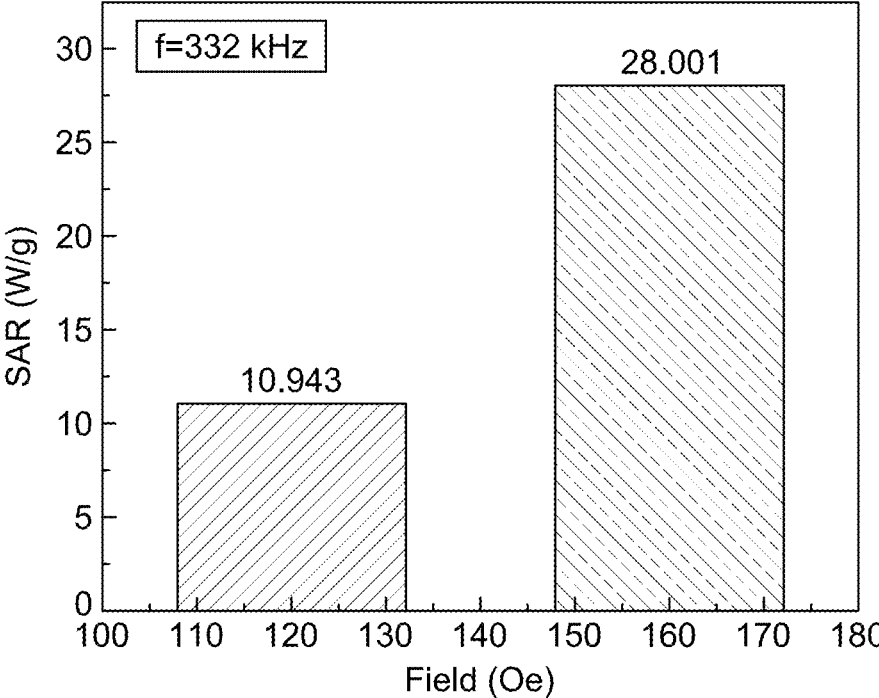
FIG. 6B is a graph depicting SAR values of the Mel-MNPs, according to certain embodiments.
Figure 7A:
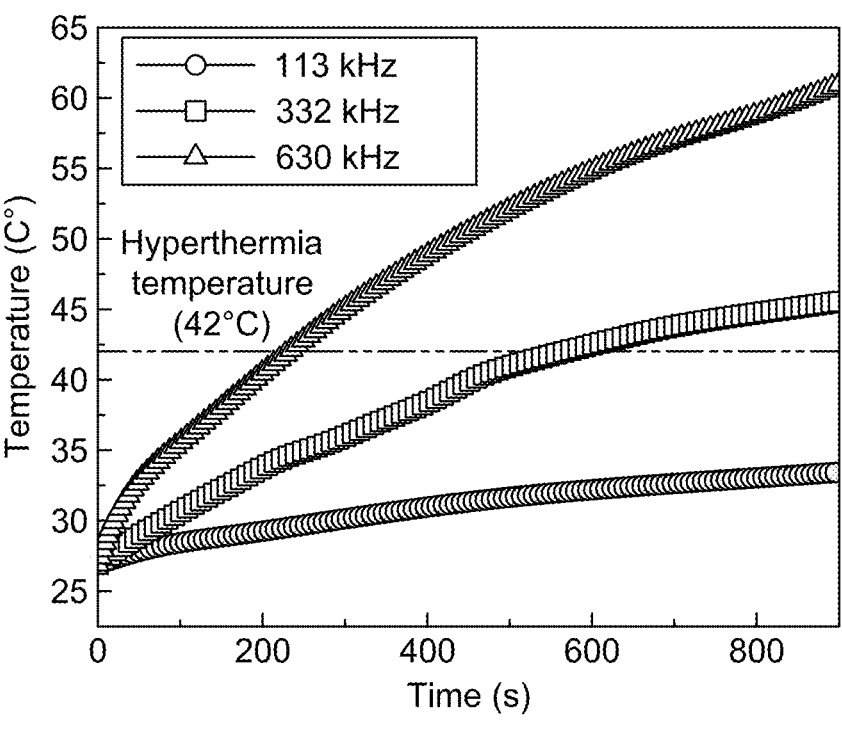
FIG. 7A is a graph depicting temperature rise for different frequencies of Mel-MNPs at a concentration of 10 mg/mL and field amplitude of 120 Oe, according to certain embodiments.
Figure 7B:
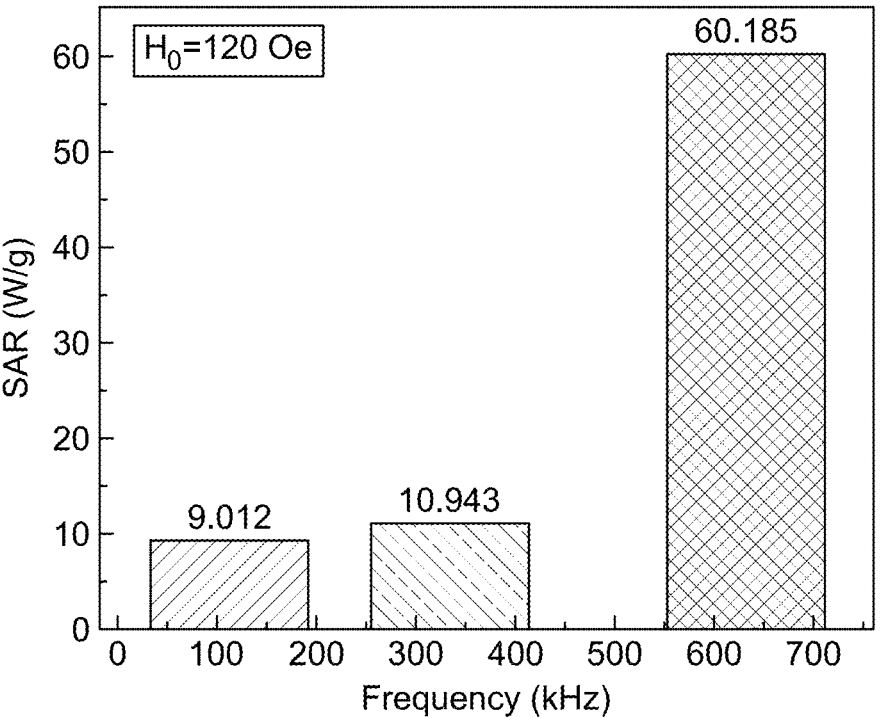
FIG. 7B is a graph depicting SAR values of the Mel-MNPs at field amplitude of 120 Oe, according to certain embodiments.

The heating efficiencies of Mel-MNPs dispersed in deionized water for the concentration of 10 mg/mL under AMF with a frequency of 332 kHz and amplitude of 160 Oe were obtained, as shown in FIG. 5A. The heating efficiency analysis satisfy the magnetic hyperthermia safety. The main heating parameters obtained from the temperature rise are summarized in Table 2. Both samples show high heating ability and reach magnetic hyperthermia temperature of 42° C. in a short time period. In an example, Mel-MNPs reached magnetic hyperthermia temperature in 4.02 minutes. The specific absorption rate (SAR) is used to quantify the heat generated by magnetic nanoparticles and can be determined by the following equation, $$SAR = \frac{\rho C_w}{M_{MNP}} \left( \frac{\Delta T}{\Delta t} \right)$$

where '$C_w$' is the water-specific heat capacity (4.185 J/g·k), '$\rho$' is the density of the colloid, '$M_{MNP}$' is the concentration of the magnetic nano-powder in the suspension, '$\Delta T/\Delta t$' is the heating rate and calculated from the slope of a linear fit of temperature increase versus time at initial time interval of 1 second to 15 seconds. The obtained values of SAR are shown in FIG. 5B. As can be seen from FIG. 5, SAR values of Mel-MNPs are considerable. In order for a logical comparison of the heating efficiency, the intrinsic loss of power (ILP) metric was used, which may be calculated by the following equation, $$ILP = \frac{SAR}{f \cdot H_0^2}$$

where 'f' is the frequency and '$H_0$' is the magnetic field. ILP values for 10 mg/mL sample of Mel-MNPs is equal to 0.520 nano-Henry square meter per kilogram (nHm²/kg). However, the ILP values are in the range reported for commercial ferrofluids which is from about 0.2 nHm²/kg to about 3.1 nHm²/kg.

TABLE 2

Heating characteristics for 10 mg/mL of pure iron oxide and Mel-MNPs at a frequency of 332 kHz and field amplitude H₀ of about 160 Oe

| Sample | Maximum temperature (° C.) | Time (min) to reach hyperthermia at 42° C. | SAR (W/g), 2 to 15 seconds | ILP (nHm²/kg) |
|---|---|---|---|---|
| Mel-MNPs | 62.09 | 4.02 | 28.001 | 0.520 |

TABLE 3

Heating characteristics for Mel-MNPs (10 mg/mL) at different field amplitudes and frequency of 332 kHz

| Field H₀ (Oe) | Maximum temperature (° C.) | Time (min) to reach hyperthermia at 42° C. | SAR (W/g), 2 to 15 seconds | ILP (nHm²/ kg) |
|---|---|---|---|---|
| 120 | 45.48 | 9.47 | 10.943 | 0.361 |
| 160 | 62.09 | 4.02 | 28.001 | 0.520 |

TABLE 4

Heating characteristics for Mel-MNPs (10 mg/mL) at different frequencies and field amplitude H₀ of 120 Oe

| Frequency (kHz) | Maximum temperature (° C.) | Time (min) to reach hyperthermia at 42° C. | SAR (W/g), 2 to 15 seconds | ILP (nHm²/kg) |
|---|---|---|---|---|
| 332 | 45.48 | 9.47 | 10.943 | 0.361 |
| 630 | 62.09 | 4.02 | 28.001 | 0.520 |

Example 5: Cell Proliferation Assay

Figure 8A:
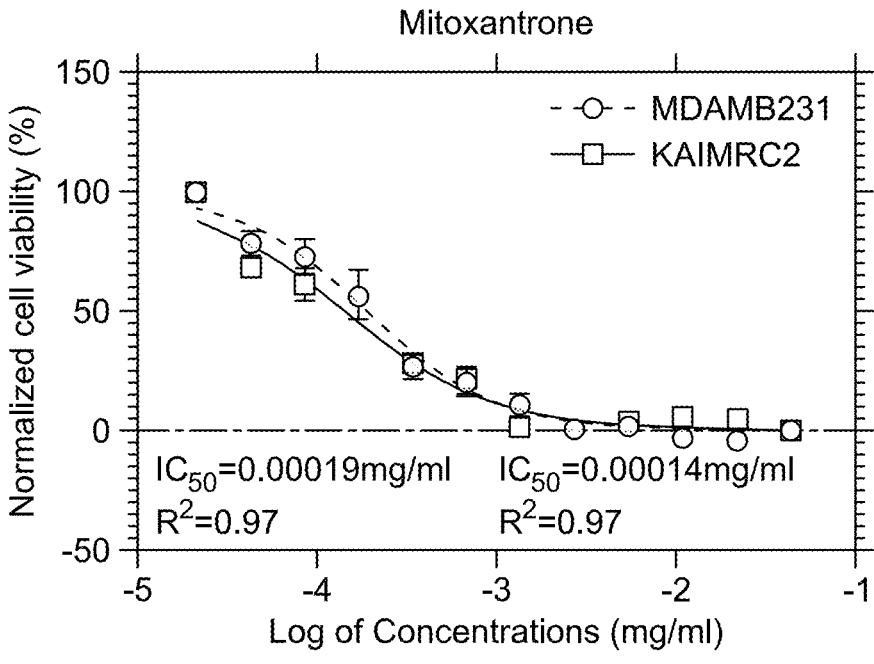
FIG. 8A is a graph depicting half maximal inhibitory concentration ($IC_{50}$) of treated breast cancer cell lines with reference drug mitoxantrone, according to certain embodiments.
Figure 8B:
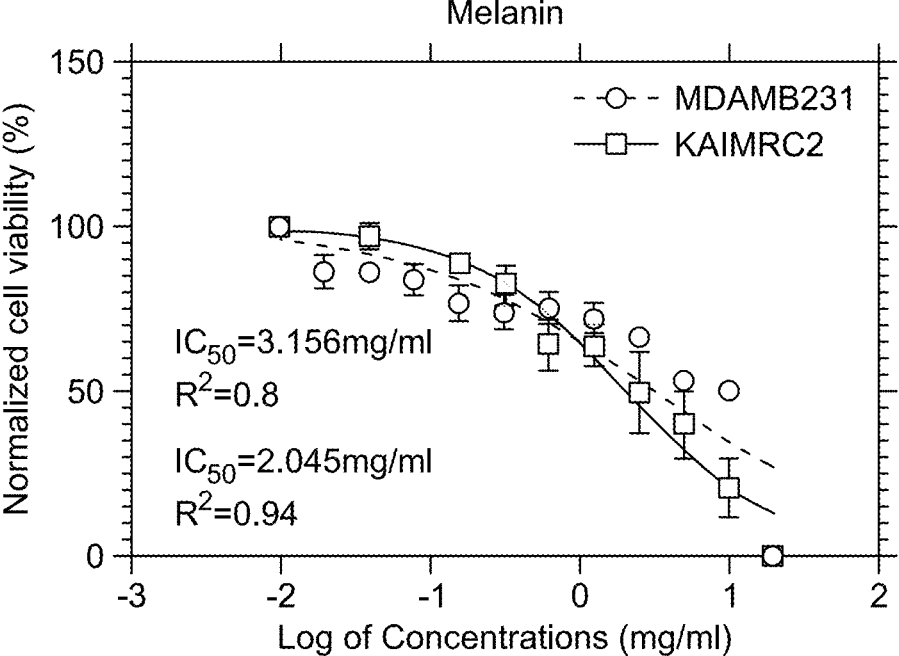
FIG. 8B is a graph depicting half maximal inhibitory concentration ($IC_{50}$) of treated breast cancer cell lines with the synthesized Mel-MNPs, according to certain embodiments.
Figure 9:
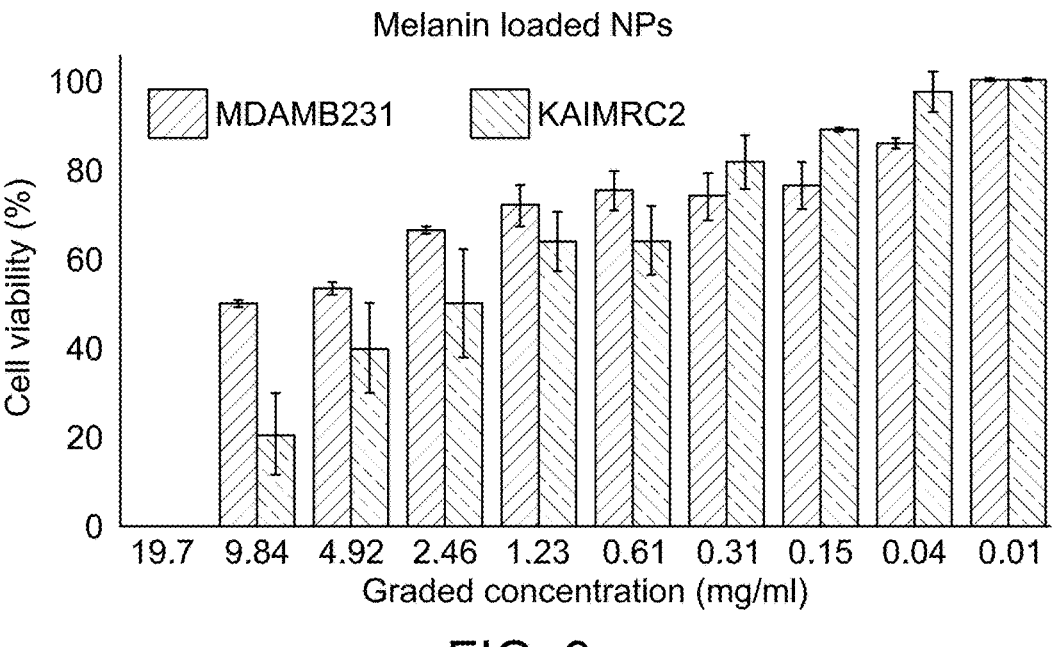
FIG. 9 is a graph depicting viability percentage of breast cancer cell lines, KAIMRC2 and MDAMB231, at different concentrations of the synthesized Mel-MNPs, according to certain embodiments.
Figure 10:
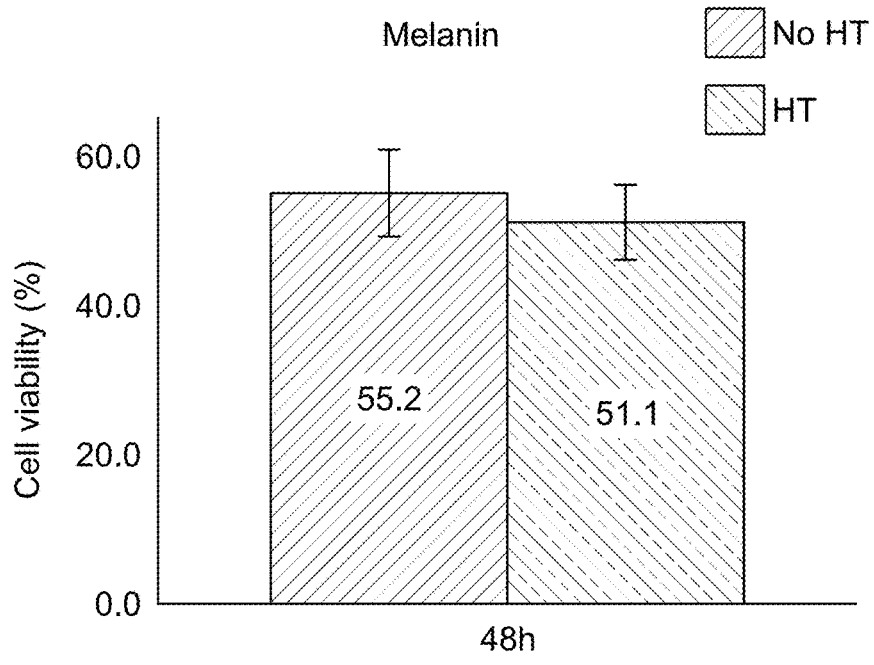
FIG. 10 is a graph depicting cellular response to hyperthermia of Mel-MNPs, according to certain embodiments.

Cell proliferation of breast cancer cells including MDAMB231 cells, and KAIMRC1 cells, exposed to the Mel-MNPs was determined using a 3-(4,5-dimethylthiazol-2-yl)-2,5-diphenyltetrazolium bromide (MTT) assay. The cell lines were seeded in a 96-well plate at a density of 5×10⁵ cells/well, and incubated in a humidified air incubator at 37° C. Following overnight incubation, cells were treated with graded concentrations of bare and melanin loaded NPs in 100 microliters (L) of supplemented Dulbecco's modified eagle medium (DMEM). Post 48 h incubation, 5 µL of MTT reagent (5 mg/mL) was added to each well and kept for 3 h at 37° C. in the incubator. Further, the media was removed, and 100 µL of dimethyl sulfoxide (DMSO) was added to each well of the 96-well plate. The absorbance was measured on a molecular device's spectrophotometer absorbance reader at 590 nm for MTT and 650 nm for control. The data was analyzed using GraphPad Prism 8 software. Cellular response to hyperthermia was determined on KAIMRC2 cells exposed to NPs at 5 mg/ml and 3 mg/ml concentrations. IC₅₀ graphs of treated breast cancer cell lines with reference drug mitoxantrone and the Mel-MNPs are shown in FIGS. 8A through 8B. The cells were treated with graded concentrations of Mel-MNPs loaded NPs. Mel-MNPs treated MDAMB231, and KAIMRC2 cell lines showed IC₅₀ of 3.156 mg/mL and 2.045 mg/mL, respectively. IC₅₀ depict that the NPs are biocompatible and non-toxic. Viability percentage of breast cancer cell lines, KAIMRC2 and MDAMB231 are presented at different concentrations of Mel-MNPs in FIG. 9. The cell viability was above 80%, even at high concentration of 0.3 mg/ml depicting that the Mel-MNPs are non-toxic and show cytotoxicity at high concentrations. Cell viability percentage of breast cancer cell line, KAIMRC2 with or without hyperthermia is presented at 5 mg/ml and 3 mg/ml concentrations of Mel-MNPs in FIG. 10. The viability of cells was decreased when the cells treated with Melanin loaded NPs were exposed to hyperthermia. The aforementioned results indicate that iron oxide is effectively encapsulated within natural melanin, regardless of exposure to hyperthermia. The encapsulation enhances the desirable properties of the material, indicating a potential for a variety of medical applications. Extracting melanin from the black seed coats of *Nigella sativa* and coating iron oxide nanoparticles for use in magnetic hyperthermia therapy has advantages due to specific chemical and structural properties. Melanin acts as a capping and stabilizing agent in nanoparticle synthesis, providing antioxidant, anti-inflammatory, and cytotoxic properties. The melanin extracted from *Nigella sativa* exhibits strong free radical scavenging abilities, which could enhance stability and reactivity in hyperthermia applications. Further, Table 5 and Table 6 lists the anti-cancer effect of the synthesized Mel-MNPs and a mitoxantrone, respectively.

TABLE 5

| Mel-MNPs results for breast cancer cell lines—MDAMB231 and KAIMRC2 | | |
| --- | --- | --- |
| Melanin | MDAMB231 | KAIMRC2 |
| Log (inhibitor) vs. normalized response- Variable slope (Best fit values) | | |
| Log $IC_{50}$ | 0.4992 | 0.3107 |
| Hillslope | −0.5448 | −0.8338 |
| $IC_{50}$ | 3.156 | 2.045 |
| 95% CI | | |
| Log $IC_{50}$ | 0.2912 to 0.7255 | 0.1903 to 0.4302 |
| Hillslope | −0.7358 to −0.4080 | −1.039 to −0.6707 |
| $IC_{50}$ | 1.955 to 5.315 | 1.550 to 2.693 |
| Goodness of fit | | |
| Degrees of freedom | 29 | 18 |
| R squared | 0.8030 | 0.9425 |
| Sum of squares | 4218 | 1176 |
| Sy.x | 12.06 | 8.082 |
| Number of points | | |
| Number of X values analysed | 36 | 36 |
| Number of Y values analysed | 31 | 20 |

TABLE 6

| Mitoxantrone results for breast cancer cell lines—MDAMB231 and KAIMRC2 | | |
| --- | --- | --- |
| Mitoxantrone | MDAMB231 | KAIMRC2 |
| Log (inhibitor) vs. normalized response- Variable slope (Best fit values) | | |
| Log $IC_{50}$ | −3.719 | −3.846 |
| Hillslope | −1.204 | −1.044 |
| $IC_{50}$ | 0.0001908 | 0.0001425 |

TABLE 6-continued

| Mitoxantrone results for breast cancer cell lines—MDAMB231 and KAIMRC2 | | |
| --- | --- | --- |
| Mitoxantrone | MDAMB231 | KAIMRC2 |
| 95% CI | | |
| Log $IC_{50}$ | −3.776 to −3.663 | −3.944 to −3.747 |
| Hillslope | −1.387 to −1.054 | −1.266 to −0.8639 |
| $IC_{50}$ | 0.0001674 to 0.0002172 | 0.0001137 to 0.0001791 |
| Goodness of fit | | |
| Degrees of freedom | 33 | 18 |
| R squared | 0.9754 | 0.9670 |
| Sum of squares | 1077 | 737.4 |
| Sy.x | 5.713 | 6.400 |
| Number of points | | |
| Number of X values analysed | 36 | 36 |
| Number of Y values analysed | 35 | 20 |

Example 6: Comparison of Mel-MNPs of Present Disclosure with Other Magnetic Particles Table 7 shows a comparison of magnetic properties and applications with different references. The biological activity was evaluated in terms of antibacterial, antioxidant (nitric oxide scavenging), antielastase, antityrosinase, antimelanogenic, and anticancer activity. The melanin from *Nigella sativa* has distinct polyphenolic compounds that may provide improved biological compatibility and reduced toxicity, especially in contrast to other sources of melanin. This melanin exhibits a high degree of biocompatibility with cells and minimal toxicity in moderate concentrations. Additionally, the specific chemical makeup of *Nigella sativa* melanin, enriched with specific polyphenolic and antioxidant molecules, improves the thermal stability and magnetic responsiveness of iron oxide nanoparticles, potentially enhancing heat generation during hyperthermia treatment as shown clearly in magnetic hyperthermia results (SAR=60.185 W/g, 630 kHz, H0=120 Oe at very short time=3.85 min) compared with other works.

TABLE 7

| Comparison of magnetic properties, type of melanin, particle size, and application with different references | | | | | | |
| --- | --- | --- | --- | --- | --- | --- |
| MNPs sample | Type of magnetism | Use | Cancer | Melanin type | Particle size (nm) | Reference |
| Mel-MNPs | Superpara-magnetic | Hyperthermia | MDAMB231 and KAIMRC1 | Herbal | 6.43 to 11.21 | Present work |
| $Fe_3O_4$ @Pheo | Superpara-magnetic | | MCF-7 cells | Chemical | 9.5 ± 14 | BR102016015484A2 |
| $Fe_3O_4$ @ mel NCs | Ferro-magnetic | Imaging and photothermal treatment | U87 MG cells | Chemical | | CN106390120 |
| euMel-$Fe_3O_4$ | Superpara-magnetic | MR & PA imaging | U-87 MG cells | Chemical | 10-12 | Al-Tayib, Omar A., et al. *"The aqueous extracts of the Nigella sativa melanin: experimental in vivo test and in vitro HEp-2 cell lines cytotoxicity effects."* IOSR |

TABLE 7-continued

Comparison of magnetic properties, type of melanin,
particle size, and application with different references

| MNPs sample | Type of magnetism | Use | Cancer | Melanin type | Particle size (nm) | Reference |
|---|---|---|---|---|---|---|
| OBX-MMNs | Ferro-magnetic | MRI | MDA-MB-231 and MDA-MB-468 | Chemical | 15 | J Agric Vet Sci 9.6 (2016): 84-90 Al-Tayib, Omar A., Samia M. ElBadwi, and Amel O. Bakhiet. *"Cytotoxicity assay for herbal melanin derived from Nigella sativa seeds using in vitro cell lines."* IOSR J. Humanit. Soc. Sci 22 (2017):43 |
| Mag-netite | Ferro-magnetic | — | Not for cancer | — | None | Aumeeruddy, Muhammad Zakariyyah, et al. *"Biological, phytochemical, and physico-chemical properties of two commercial Nigella sativa seed oils: A comparative analysis."* Istanbul Journal of Pharmacy 48.3 (2019): 89-99. |

Numerous modifications and variations of the present disclosure are possible in light of the above teachings. It is, therefore, to be understood that within the scope of the appended claims, the invention may be practiced otherwise than as specifically described herein.

The invention claimed is:

1. A method of treating a breast cancer with magnetic hyperthemia therapy, comprising:

producing melanin-coated magnetite nanoparticles (Mel-MNPs) comprising a *Nigella sativa*-derived melanin;

contacting the Mel-MNPs with the breast cancer; and applying an external alternating magnetic field to the Mel-MNPs to generate heat to hyperthermically treat the breast cancer, wherein the cancer treatment inhibits the proliferation of at least one breast cancer cell line selected from the group consisting of MDAMB231 and KAIMRC1 compared to a control cancer cell line that is not treated;

wherein the Mel-MNPs have a magnetic coercivity ($H_C$) of 4.5 to 6.5 Oersted (Oe); and wherein the Mel-MNPs have a remanence of 0.05 to 1 emu/g.

2. The method of claim 1, wherein the Mel-MNPs have an average particle diameter of 20 nm or less.

3. The method of claim 1, wherein the contacting comprises administering a composition comprising the Mel-MNPs in a concentration of at least 3 mg/mL to the cancer.

4. The method of claim 1, wherein the at least one breast cancer cell line is MDAMB231.

5. The method of claim 1, wherein the at least one breast cancer cell line is KAIMRC1.

6. The method of claim 1, wherein the external alternating magnetic field has a frequency of 300 to 700 kHz.

7. The method of claim 1, wherein the Mel-MNPs have an average particle diameter of 16 nm or less.

8. The method of claim 1, further comprising:

solubilizing black seed coats of *Nigella sativa* in an NaOH solution for at least 2 hours to obtain an extract solution;

centrifuging the extract solution at a rate of 1000 to 4000 rpm for 1 to 10 minutes, then adding an HCl solution to obtain a precipitate; and filtering the precipitate to obtain the *Nigella sativa*-derived melanin.

9. The method of claim 1, wherein the Mel-MNPs have a saturation magnetization ($M_s$) of 6.5 to 9 emu/g.

10. The method of claim 1, wherein the contacting comprises administering a composition comprising the Mel-MNPs in a concentration of at least 10 mg/mL to the cancer.

11. The method of claim 1, wherein the contacting comprises applying of the external alternating magnetic field to the at a frequency of 300 to 700 kHz until the cancer achieves an internal temperature of at least 45° C. in 10 minutes or less.

12. The method of claim 1, wherein the applying of the external alternating magnetic field to the Mel-MNPs at a frequency of 300 to 700 kHz until the cancer achieves an internal temperature of the cancer of at least 55° C. in 5 minutes or less.

13. The method of claim 1, wherein the Mel-MNPs are made by a process comprising:

heating an aqueous metal chloride mixture to a temperature of 60° C. to 100° C. and reacting the aqueous metal chloride mixture with an ammonia hydroxide solution to obtain metal oxide nanoparticles; and sonicating a buffered aqueous suspension of the metal oxide nanoparticles and a *Nigella sativa*-derived melanin to obtain the Mel-MNPs.

14. The method of claim 13, wherein the aqueous metal chloride mixture comprises at least one metal chloride selected from the group consisting of $FeCl_3$, $FeCl_2$, $CoCl_2$, KCl, $NH_4Cl$, $MgCl_2$, NaCl, $BrCl_2$, $CaCl_2$, $NiCl_2$, and $SrCl_2$.

15. The method of claim 13, wherein the aqueous metal chloride mixture comprises at least one metal chloride selected from the group consisting of $FeCl_3$ and $FeCl_2$.

16. The method of claim 13, wherein the buffered aqueous suspension comprises at least one selected from the group consisting of (4-(2-hydroxyethyl)-1-piperazineethanesulfonic acid (HEPES), 3-(N-morpholino)propanesulfonic acid (MOPS), and tris(hydroxymethyl)aminomethane hydrochloride (TRIS—HCl).

17. The method of claim 13, wherein the sonicating comprises sonicating the buffered aqueous suspension for 10 to 40 minutes at a frequency of 15 to 50 kHz to obtain the Mel-MNPs.

18. The method of claim 13, wherein the buffered aqueous suspension comprises a weight ratio of metal oxide nanoparticles to *Nigella sativa*-derived melanin of 1:15 to 15:1.

19. The method of claim 13, wherein the buffered aqueous suspension comprises a weight ratio of metal oxide nanoparticles to *Nigella sativa*-derived melanin of 10:1.

20. The method of claim 1, wherein the Mel-MNPs have a magnetic coercivity ($H_C$) of 5.55 to 5.6 Oersted (Oe); and have a remanence of 0.05 to 0.75 emu/g, wherein said Mel-MNP exhibits a rising hysteresis curve.

\* \* \* \* \*